US007723361B2

(12) United States Patent
D'Amato

(10) Patent No.: US 7,723,361 B2
(45) Date of Patent: *May 25, 2010

(54) METHODS FOR INHIBITING UNDESIRED ANGIOGENESIS IN PATIENTS HAVING TUMORS WITH THALIDOMIDE

(75) Inventor: Robert D'Amato, Lancaster, PA (US)

(73) Assignee: Celgene Corporation, Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/096,155

(22) Filed: Mar. 31, 2005

(65) Prior Publication Data

US 2005/0215593 A1    Sep. 29, 2005

Related U.S. Application Data

(60) Division of application No. 09/704,054, filed on Nov. 1, 2000, which is a division of application No. 09/545,139, filed on Apr. 7, 2000, now Pat. No. 6,469,045, which is a division of application No. 08/950,673, filed on Oct. 16, 1997, now Pat. No. 6,071,948, which is a continuation of application No. 08/468,792, filed on Jun. 6, 1995, now Pat. No. 5,712,291, which is a continuation of application No. 08/168,817, filed on Dec. 15, 1993, now Pat. No. 5,629,327, which is a continuation-in-part of application No. 08/025,046, filed on Mar. 1, 1993, now abandoned.

(51) Int. Cl.
*A61K 31/445* (2006.01)
(52) U.S. Cl. ................................... 514/323
(58) Field of Classification Search ................ 514/323
See application file for complete search history.

(56) References Cited

U.S. PATENT DOCUMENTS

| 2,830,991 | A | 4/1958 | Keller et al. |
| 3,560,495 | A | 2/1971 | Frankus et al. |
| 3,563,986 | A | 2/1971 | Frankus et al. |
| 3,625,946 | A | 12/1971 | Koch et al. |
| 3,705,162 | A | 12/1972 | Graudums et al. |
| 4,552,888 | A | 11/1985 | Koppel et al. |
| 4,808,402 | A | 2/1989 | Leibovich et al. |
| 4,994,443 | A | 2/1991 | Folkman et al. |
| 5,001,116 | A | 3/1991 | Folkman et al. |
| 5,021,404 | A | 6/1991 | Folkman et al. |
| 5,134,127 | A | 7/1992 | Stella et al. |
| 5,260,329 | A | 11/1993 | Mongelli et al. |
| 5,399,363 | A | 3/1995 | Liversidge et al. |
| 5,434,170 | A | 7/1995 | Andrulis, Jr. |
| 5,502,066 | A | 3/1996 | Heinemann et al. |
| 5,605,914 | A | 2/1997 | Muller |
| 5,629,327 | A | 5/1997 | D'Amato |
| 5,635,517 | A | 6/1997 | Muller et al. |
| 5,643,915 | A | 7/1997 | Andrulis, Jr. et al. |
| 5,654,312 | A | 8/1997 | Andrulis, Jr. et al. |
| 5,679,696 | A | 10/1997 | Fenton et al. |
| 5,731,325 | A | 3/1998 | Andrulis, Jr. et al. |
| 6,140,346 | A | 10/2000 | Andrulis, Jr. et al. |

FOREIGN PATENT DOCUMENTS

| EP | 0325199 | 7/1989 |
| EP | 0357061 | 3/1990 |
| GB | 1182709 | 3/1970 |
| WO | WO 92/14455 | 9/1992 |
| WO | WO 92/18496 | 10/1992 |
| WO | WO 95/04533 | 2/1995 |

OTHER PUBLICATIONS

Thomas et al. Current role of thalidomide in cancer treatment. Current Opinion in Oncology, 2000, 12:564-573.*
Gutman et al. Failure of thalidomide to inhibit tumor growth and angiogenesis in vivo. Anticancer Research, 1996, 16:3673-3677.*
Arand et al. Methods in Enzymology, 2005, vol. 400, pp. 569-588.*
Fretland et al. Chemico-Biological Interactions, 2000, vol. 129, pp. 41-59.*
Allegri, Gazz. Med. Ital., 123 (1964), pp. 124-127.
Bach, The Lancet, "Thalidomide in Cancer Chemotherapy", No. 1271, pp. 71 (1963).
Bach, Acta Pathologica Et Microbiologica Scandinavica, "Studies on the Possible Anti-Neoplastic Effect of Thalidomide", No. 59, pp. 491-499 (1963).
Chaundhry, Cancer Research, "Effect of Prednisolone and Thalidomide on Induced Submandibular Gland Tumors in Hamster", 26 part 1, pp. 1884-1886 (1966).
DiPaolo, Cancer Chemotherapy Reports, "Effect of Thalidomide on a Variety of Transplantable Tumors", No. 29, pp. 99-102 (1963).
DiPaolo, Proceedings of the Society for Experimental Biology & Medicine, "In vitro Test Systems for Cancer Chemotherapy, II. Correlation of in vitro Inhibition of Dehydrogenase and Growth with in vivo Inhibition of Enrlich Asoites Tumor", 114, pp. 384-387 (1963).
DiPaolo, "Thalidomide: Effects on Ehrlich Ascites Tumor Cells in vitro" (1964).
Gaetani, Giorn. Ital. Chimioter., 11, pp. 83-86 (1964).
Gershbein, Cancer Letters, "The Thalidomide Analog, EM 12, Enhances 1,2-Dimethylhydrazine-Induction of Rat Colon Adenocarcinomas," 60, pp. 129-133 (1991).
Grabstald and Golbey, 1965, "Clinical experiences with thalidomide in patients with cancer", Clinical Pharmacology and Therapeutics, 6:298-302.

(Continued)

*Primary Examiner*—James D Anderson
(74) *Attorney, Agent, or Firm*—Jones Day

(57) ABSTRACT

The present invention comprises a group of compounds that effectively inhibit angiogenesis. More specifically, thalidomide and various related compounds such as thalidomide precursors, analogs, metabolites and hydrolysis products have been shown to inhibit angiogenesis and to treat disease states resulting from angiogenesis. Importantly, these compounds can be administered orally.

7 Claims, 5 Drawing Sheets

OTHER PUBLICATIONS

Juret et al., Seances Soc. Biol. Filial., 157, pp. 246-249 (1963).
Koch, Progress in Medicinal Chemistry, "Thalidomide and Congeners as Anti-Inflammatory Agents", 22, pp. 165-242, (1985).
Mau'ad MJ., Anais Paulistas de Medicina e Cirurgia, "Clinical Improvements Obtained in Advanced Cancer Patients with Treatment with Thalidomide Associated with Hormones", 86, pp. 13-40 (1965).
Miller et al., Monatsschr. Kinderheilk, 128, pp. 27-29 (1980).
Miura et al., Experientia, 26, pp. 305-306 (1970).
Muckter H., 1965, "Thalidomide and Tumor", Antimicrobial Agents and Chemotherapy 531-8.
Olson et al., Clinical Pharmacology and Therapeutics, "Thalidomide (N-phthaloylglutamimide) in the Treatment of Advanced Cancer", 6(3), pp. 292-297 (1965).
Pagnini et al., Boll. Soc. Ital. Biol. Sperim., 39, pp. 1360-1363 (1963).
Roe et al., Nature, "Thalidomide on Induced Submandibular Gland Tumors in Hamster", 200, pp. 1016-1017 (1963).
Sugiura et al., "Effect of Thalidomide on Transplantable Mouse, Rat and Hamster Tumors" Gann, 55, 57-60.
Traldi et al., Cancro, 18 (1965), pp. 336-341.
Woodyatt, Lancet, 1962, pp. 750, "Thalidomide".
Schulze-Osthoff, K. et al, Am. J. Pathol. 1990, 137(1), pp. 85-92.
Allegri, A., "Confermata l'inefficacia della Talidomide Nella Terapia dei Tumori", Gazzetta Medica Italiana, pp. 124-127 (1964).
Aronson, et al., "Thalidomide-Induced Peripheral Neuropathy. Effect of Serum Factor on Nerve Cultures", Arch. Dermatol., vol. 120, No. 11, pp. 1466-1470 (1984).
Balabanova, et al., "Lupus Erythermatosus Hypertrophicus et Profundus", Z. Hautkr., vol. 67, No. 9, pp. 812-815 (1992).
Barnhill, et al., "Thalidomide: Use and Possible Mode of Action in Reactional Lepromatous Leprosy and in Various Other Conditions", J. Am. Acad. Dermatol., vol. 7, No. 3, pp. 317-323 (1982).
Beccerica, E., "L'approccio terapeutico al paziente anziano con artrite reumatoide", Clin. Ter., vol. 122, pp. 289-298 (1987).
Bensinger, W.I., "Supportive Care in Marrow Transplantation", Curr. Opin. Oncol., vol. 4, No. 4, pp. 614-623 (1992).
Bonnetblanc, et al., "Thalidomide and Recurrent Aphthous Stomatitis: a Follow-up Study", Dermatology, vol. 193, No. 4, pp. 321-323 (1996).
Boodman, S.G., "Questions About a Popular Prenatal Test", The Washington Post (1992).
Bowers, et al., "Effect of Thalidomide on Orogenital Ulceration", Br. Med. Journ., vol. 287, No. 6395, pp. 799-800 (1983).
Braun, et al., "Thalidomide Metabolite Inhibits Tumor Cell Attachment to Concanavalin a Coated Surfaces", Biochem. Biophys. Res. Comm., vol. 98, No. 4, pp. 1029-1034 (1981).
Brodthagen, H., "Significant Response of Oral Aphthosis to Thalidomide Treatment", J. Am. Acad. Dermatol., vol. 13, No. 3, p. 509 (1985).
Brovarone, et al., "Occhio e gravidanza", Minerva Ginecol., vol. 43, pp. 141-167 (1991).
Bubl, et al., "Dysphagia in Dermatologic Disease", Dysphagia, vol. 8, No. 2, pp. 85-90 (1993).
Bullock, W.E., "The Clinical Significance of Erythema Nodosum", Hosp. Pract., vol. 21, No. 3, pp. 102E-102H, 102K-102L, 102Q-102R pas (1986).
Burger, et al., "Epidermolysis Bullosa Acquisita, a Rare Late Complication of Allogeneicbone Marrow Transplantation?", Bone Marrow Transplant, vol. 9, No. 2, pp. 139-141 (1992).
Calnan, et al., "Actinic Prurigo (Hutchinson's Summer Prurigo)", Clin. Exp. Dermatol., vol. 2, No. 4, pp. 365-372 (1977).
Cant, J.S., "Minor Ocular Abnormalities Associated With Thalidomide", The Lancet, p. 1134 (1966).
Carmichael, et al., "Thalidomide: A Restricted Role", Lancet, vol. 339, No. 8805, p. 1362 (1992).
Chapon, et al., "Neuropathies Caused by Thalidomide", Rev. Neurol., vol. 141, No. 11, pp. 719-728 (1985).
Chosidow, O, et al., "Sclerodermatous Chronic Graft-Versus-Host-Disease: Analysis of Sevencases", J. Am. Acad. Dermatol., vol. 26, No. 1, pp. 49-55 (1992).
Claydon, et al., "Gastrointestinal Emergencies in HIV Infection", Balliere's Clin Gastroennterol., vol. 5, No. 4, pp. 887-911 (1991).
Clemmensen, et al., "Thalidomide Neurotoxicity", Arch. Dermatol, vol. 120, No. 3, pp. 338-341 (1984).
Congy, et al., "Plasma Zinc Levels in Elderly Patients Hospitalized in Long Stay Units. Correlations with Other Nutritional Markers, Immunological Tests and Survival", Sem. Hop. Paris, vol. 59, No. 45, pp. 3105-3108 (1983).
Costa, et al., "Aseptic Adenitis in a Patient with Pyoderma Gangrenosum", Ann. Dermatol., vol. 121, No. 8, pp. 550-552 (1994).
Crawford, C.L., "Letter: Thalidomide in Erythema Nodosum Leprosum", Lancet, vol. 2, No. 839, pp. 1201-1202 (1973).
Crawford, C.L., "Treatment of Erythema Nodosum Leprosum with Thalidomide", Lancet, vol. 2, No. 828, pp. 567-568 (1973).
Crawford, C.L., "Use of Thalidomide in Leprosy [letter; comment]", BMJ, vol. 302, No. 6729, pp. 1603-1604 (1991).
Current Bibliographies in Medicine, "Thalidomide: Potential Benefits and Risks", National Inst. Health, National Library of Medicine, pp. 1-72 (Jan. 1963-Jul. 1997).
D'Amato, et al., "Angiogenesis Inhibition in Age-Related Macular Degeneration", Opthalmology, vol. 102, No. 9, pp. 1261-1262 (1995).
D'Amato, et al., "Microscopic Analysis of Retinal-Vessels Utilizing Fluorescein-Labeled High-Molecular-Weight Dextrans", Invest. Opthamol. & Visual Science, vol. 33, No. 4, p. 1082 (1992).
Dark, et al., "Combretastin A-4, an Agent that Displays Potent and Selective Toxicity Toward Tumor Vasculature", Cancer Research, vol. 37, pp. 1829-1834 (1997).
David-Bajar, K.M., "Subacute Cutaneous Lupus Erythematosus", J. Invest. Dermatol. vol. 100, No. 1, pp. 2s-8s (1993).
DeKlerk, et al., "New Methods of Treatment for Renal Allotransplants Using the Baboon as a Primate Experimental Model", J. Urol. vol. 102, No. 5, pp. 532-540 (1969).
DiPaolo, et al., "Thalidomide: Effects on Ehrlich Ascites Tumor Cells in vitro", Science, vol. 144, pp. 1583 (1964).
DiPaolo, "Effect of Thalidomide on a Variety of Transplantable Tumors", Cancer Chemo. Reports, vol. 29, pp. 99-102 (1963).
DiPaolo, "In Vitro Test Systems for Cancer Chemotheraphy. II. Correlation of In Vitro Inhibition of Dehydrogenase and Growth with In Vivo Inhibition of Ehrlich Ascites Tumor", P.S.E.B.M., vol. 114, pp. 384-387 (1963).
DiPaolo et al., "Teratogenesis-oncogenesis: A Study of Possible Relationships", Arch. Path., vol. 81, pp. 3-23 (1966).
Dorveaux, et al., "Le Traitement Actuell du Lupus Erythemateux Chronique", Le Concours Med. vol. 106, No. 31, pp. 2957-2961 (1984).
Doutre, et al., "Pyoderma Gangrenosum and Hemopathies. A propos of 2 Cases", Nouv Rev Fr Hematol, vol. 29, No. 4, pp. 251-254 (1987).
Dunn, et al., "Bone Marrow Transplantation and Cataract Development", Arch. Ophthalmol. vol. III, No. 10, pp. 1367-1373 (1993).
(Editorial) "Thalidomide in Dermatology and Leprosy", Lancet, vol. 2, No. 8446, pp. 80-81 (1985).
(Editorial) "Thalidomide Tested for Treatment of AIDS", U.S. Pharm., vol. 18, No. 8, p. 14 (1993).
Elia, et al., "Giant Esophageal Ulcer Treated with Steroids in AIDS Patient(2)", J. Acquired Immune Defic. Syndr., vol. 5, No. 8, pp. 848-849 (1992).
Eriksson, et al., "Drug Exposure and Flow Cytometry Analyses in a Thalidomide Treatment Schedule that Prolongs Rat Cardiac Graft Survival", Transplant Proc., vol. 24, No. 6, pp. 2560-2561 (1992).
Fajardo, et al., "Dual Role of Tumor Necrosis Factor-.alpha. in Angiogenesis", Am. J. Pathol., vol. 140, No. 3, pp. 539-544 (1992).
Faure, et al., "PMN Leukocytes Chemotaxis: Inhibition by Thalidomide", Pathol. Biol. (Paris), vol. 29, No. 10, pp. 601-604 (1981).
Faure, et al., "Inhibition of PMN Leukocytes Chemotaxis by Thalidomide", Arch. Dermatol. Res., vol. 269, No. 3, pp. 275-280 (1980).
Francois, J., "Embryological Pigment Epithelial Dystrophies", Opthalmologica, vol. 172, pp. 417-433 (1976).
Fuller, et al., "Thalidomide, Peripheral Neuropathy and AIDS", Int. J. STD AIDS, vol. 2, No. 5, pp. 369-370 (1991).

Furner, B.B., "Treatment of Subacute Cutaneous Lupus Erythematosus", Int. J. Dermatol., vol. 29, No. 8, pp. 542-547 (1990).
Gad, et al., "Thalidomide Induces Imbalances in T-Lymphocytes Sub-Populations in the Circulating Blood of Healthy Males", Lepr. Rev., vol. 56, No. 1, pp. 35-39 (1985).
Gehanno, et al., "Mouth and Pharyngeal Hyperalgesic Syndromes in AIDS", Ann. Otolarygol Chir. Cervicofac, vol. 107, No. 5, pp. 311-313 (1990).
Genvo, et al., "Treatment of Aphthosis with Thalidomide and with Colchicine", Dermatologica, vol. 168, No. 4, pp. 182-188 (1984).
Geoghiou, et al., "HIV-Associated Oesophageal Ulcers Treated with Thalidomide", Med. J. of Australia, vol. 152, pp. 382-383 (1990).
Gershbein, "Effect of Transplanted Tumor and Various Agents on Liver Regeneration During Pregnancy", P.S.E.B.M., vol. 126, pp. 88-92 (1967).
Goihman-Yahr, M., et al., "Autoimmune Diseases and Thalidomide II. Adjuvant Disease, Experimental Allergic Encephalomyelitis and Experimental Allergic Neuritis of the Rat", Int. J. Leprosy, vol. 42, No. 3, pp. 266-275 (1974).
Gorin, I., et al., "Thalidomide May Cure AIDS Ulcers", Nurs. Times, vol. 86, No. 24, p. 10 (1990).
Gorin, I., et al., "Thalidomide in Hyperalgic Pharyngeal Ulceration of AIDS", Lancet, vol. 335, p. 1343 (1990).
Goulden, V., et al., "Linear Prurigo Simulating Dermatitis Artefacta in Dominant Dystrophicepidermolysis Bullosa", Br. J. Dermatol., vol. 129, No. 4, pp. 443-446 (1993).
Grinspan, et al., "Treatment of Aphthae with Thalidomide", J. Am. Acad. Dermatol., vol. 20, No. 6, pp. 1060-1063 (1989).
Grosshans, E., et al., "Thalidomide Therapy for Inflammatory Dermatoses", Int. J. Dermatol., vol. 23, No. 9, pp. 598-602 (1984).
Guidetti, E., et al., "Ricerche Sull'azione Immunodepressiva Della Talidomide e del Prednisolone in Ratti Portatori Di Neoplasie Sperimentalmente Indotte", Cancro, vol. 22, pp. 503-512 (1969).
Gunzler, V., "Thalidomide in Human Immunodeficiency Virus (HIV) Patients. A Review of Safety Considerations", Drug Saf, vol. 7, No. 2, pp. 116-134 (1992).
Hamza, M.H., "Treatment of Behcet's Disease with Thalidomide", Clinical Rheumatol., vol. 5, No. 3, pp. 365-371 (1986).
Harindra, et al., "Papulo-Pruritic Eruption and Giant Ulceration of the Mouth: A Difficult Clinical Feature to Treat in the Patient Infected with Humanimmunodeficiency Virus(1)", Arch. Intern. Med., vol. 152, No. 9, p. 1924 (1992).
Hasper, M.F., "Chronic Cutaneous Lupus Erythematosus. Thalidomide Treatment of 11 Patients", Arch. Dermatol, vol. 19, No. 10, pp. 812-815 (1983).
Hasper, M.F., et al., "Thalidomide in the Treatment of Chronic Discoid Lupus", Acta. Derm. Venereol, vol. 62, No. 4, pp. 321-324 (1982).
Hastings, R.C., et al., "Thalidomide in the Treatment of Erythema Nodosum Leprosum. With a Note on Seleted Laboratory Abnormalities in Erythema Nodosum Leprosum", Clin. Pharmacol. Ther., vol. 11, No. 4, pp. 481-487 (1970).
Heaton, et al., "Graft-versus-Host Disease Following Liver Transplantation", J. R. Soc. Med., vol. 85, No. 6, pp. 313-314 (1992).
Heney, D., et al., "Thalidomide in the Treatment of Graft-versus-Host Disease", Biomed. Pharmacother, vol. 44, No. 4, pp. 199-204 (1990).
Heney, D., et al., "Thalidomide for Chronic Graft-versus-Host Disease in Children", Lancet, vol. 2, No. 8623, p. 1317 (1988).
Hojyo, et al., "Actinic Prurigo (9)", Int. J. Dermatol., vol. 31, No. 5, pp. 372-373 (1992).
Holm, et al., "Chronic Cutaneous Lupus Erythematosus Treated with Thalidomide", Arch. Dermatol., vol. 129, No. 12, pp. 1548-1550 (1993).
Hu, D.E., "Inhibition of Angiogenesis in Rats by IL-1 Receptor Antagonist and Selected Cytokine Antibodies", Inflammation, vol. 18, pp. 45-58 (1994).
Ingber, D., "Drug News and Trial Developments", AIDS Patient Care, vol. 6, No. 6, p. 288 (1992).
Randall, T., "Thalidomide's Back in the News, but in more Favorable Circumstances", JAMA, vol. 263, No. 11, pp. 1467-1468 (1990).
Jacobson, et al., "The Diagnosis and Treatment of Leprosy", South Med. J., vol. 69, No. 8, pp. 979-985 (1976).
Jager, et al., "Clinical Observations in the Treatment of Leprosy Reaction with Cyclic Imides", Int. J. Lepr. Other Mycobact Dis., vol. 39, No. 2, p. 589 (1971).
Jenkins, et al., "Thalidomide, Orogenital Ulcers, and Risk of Teratogenicity", The Lancet, vol. 1, No. 8417-18, p. 511 (1985).
Jenkins, et al., "Thalidomide in Severe Orogenital Ulceration", The Lancet, vol. 2, No. 8417-18, pp. 1424-1426 (1984).
Jennings, et al., "Effect of Actinomycin D on the Production of Acute Phase Protein in the Rabbit", Experienta, vol. 25, pp. 305-306 (1969).
Jew, et al., "Thalidomide in Erythema Nodosum Leprosum", DICP, vol. 24, No. 5, pp. 482-483 (1990).
Jorizzo, et al., "Thalidomide Effects in Behcet's Syndrome and Pustular Vasculitis", Arch. Intern. Med., vol. 146, No. 5, pp. 878-881 (1986).
Kaitin, K.I., "Graft-versus-Host Disease", N. Engl. J. Med., vol. 325, No. 5, pp. 357-358 (1991).
Katsuta, et al., "Carcinogenesis in Tissue Culture. 3. Effects of the Second Treatments on DAB-Induced Proliferating Liver Cells of Normal Rats in Culture", Jpn. J. Exp. Med., vol. 35, No. 4, pp. 231-248 (1965).
Knop, et al., "Thalidomide in the Treatment of Sixty Cases of Chronic Discoid Lupus Erythematosus", Br. J. Dermatol, vol. 108, No. 4, pp. 461-466 (1983).
Korn, et al., "The Second International Workshop on Scleroderma Research", Matrix, vol. 13, No. 5, pp. 427-429 (1993).
Kroger, et al., "Synergistic Effects of Thalidomide and Poly (ADP-ribose) Polymerase Inhibition on Type II Collagen-Induced Arthritis in Mice", Inflammation, vol. 20, No. 2, pp. 203-215 (1996).
Kundu, et al., "Prurigo Nodularis in an HIV Positive Man (2)", Genitourinary Medicine, vol. 71, No. 2, pp. 129-130 (1995).
Lane, et al., "Treatment of Actinic Prurigo with Intermittent Short-Course Topical 0.05% Clobetasol 17-Propionate. A Preliminary Report", Arch. Dermatol, vol. 126, No. 9, pp. 1211-1213 (1990).
Languillon, J., "The Effects of Thalidomide on Leprosy Reaction", Int. J. Lepr. Other Mycobact. Dis., vol. 39, No. 2, pp. 590-592 (1971).
Ledo, E., "Photodermatosis. Part I: Photobiology, Photoimmunology, and Idiopathicphotodermatoses", Int. J. Dermatol., vol. 32, No. 6, pp. 387-396 (1993).
Lehner, T., et al., "Thalidomide, Orogenital Ulcers, and the Risk of Teratogenesis", The Lancet, vol. 8423, pp. 288-289 (1985).
Levy, et al., "Treatment of Erythema Nodosum Leprosum with Thalidomide", The Lancet, vol. 2, No. 824, pp. 324-325 (1973).
Lenicque, "Action of Thalidomide on the Induction of Tentacles in Regenerating *Hydra littoralis*", Acta. Zool., pp. 127-139 (1967).
Lo, et al., "Treatment of Discoid Lupus Erythematosus", Int. J. Dermatol., vol. 28, No. 8, pp. 497-507 (1989).
Londono, F., "Thalidomide in the Treatment of Actinic Prurigo", Int. J. Dermatol., vol. 12, No. 5, pp. 326-328 (1973).
Lovell, et al., "Thalidomide in Actinic Prurigo", Br. J. Dermatol, vol. 108, No. 4, pp. 467-471 (1983).
Magana-Garcia, M., "Antimalarials for Children", J. Am. Acad. Dermatol, vol. 30, No. 3, p. 510 (1994).
Mascaro, et al., "Thalidomide in the Treatment of Recurrent, Necrotic, and Giant Mucocutaneous Aphthae and Aphthosis", Arch. Dermt., vol. 115, pp. 636-637 (1979).
Matsubara, et al., "Inhibition of Human Endothelial Cell Proliferation by Gold Compounds", J. Clin. Invest., vol. 79, pp. 1440-1446 (1987).
Mauad, "Melhoras Clinicas Obtidas em Doentes Cancerosos Avan. cedilla.ados com Tratamento Pela Talidomida Associada a Hormonios", Anais Paulistas Medicina e Cirurgia, pp. 15-39 (1963).
Maurice, et al., "The Effect of Thalidomide on Arachidonic Acid Metabolism in Human Polymorphonuclear Leukocytes and Platelets", Br. J. Dermatol., vol. 115, No. 6, pp. 677-680 (1986).
McCarthy, et al., "Thalidomide for the Therapy of Graft-versus-Host Disease Following Allogeneic Bone Marrow Transplantation", Biomed. Pharmacother, vol. 43, No. 9, pp. 693-697 (1989).
McKenna, et al., "Linear IgA Disease, Oral Ulceration and Crohn's Disease", Br. J. Dermatol., vol. 127, pp. 67-68 (1992)
Miller, et al., "Treatment of Chronic Erythema Nodosum Leprosum with Cyclosporine A Produces Clinical and Immunohistologic Remission", Int. J. Lepr. Other Mycobact. Dis., vol. 55, No. 3, pp. 441-449 (1987).

Miyachi, Y., "A Possible Mechanism of Action of Thalidomide on Rheumatoid Arthritis", Arthritis and Rheuma., vol. 28, No. 7, p. 836 (1985).

Miyachi, et al., "Effects of Thalidomide on the Generation of Oxygen Intermediates by Zymosan-Stimulated Normal Polymorphonuclear Leukocytes", Arch. Dermatol. Res., vol. 274, Nos. 3-4, pp. 363-367 (1982).

Mohri, et al., "Negative Effect of Thalidomide and Relative Substances on the Growth of HeLa Cells", Chem. Pharm. Bull., vol. 16, pp. 2289-2292 (1968).

Moncada, et al., "Thalidomide—Effect on T Cell Subsets as a Possible Mechanism of Action", Int. J. Lepr. Other Mycobact. Dis., vol. 53, No. 2, pp. 201-205 (1985).

Montrucchio, et al., "Tumor Necrosis Factor .alpha.-Induced Angiogenesis Depends on In Situ Platelet-Activating Factor Biosynthesis", J. Exp. Med., vol. 180, pp. 377-382 (1994).

Mshana, et al., "Thymus-Dependent Lymphocytes in Leprosy. II. Effect of Chemotherapy on T-Lymphocyte Subpopulations", J. Clin. Immunol., vol. 2, No. 2, pp. 69-74 (1982).

Muckter, et al., "Thalidomide and Tumor", Antimicrobial Agents and Chemotherapy, pp. 531-538 (1965).

Munro, et al., "Pyoderma Gangrenosum Associated with Behcet's Syndrome-Response to Thalidomide", Clin. Exp. Dermatol., vol. 13, No. 6, pp. 408-410 (1988).

Moulin, et al., "Treatment of Jessner-Kanof Disease with Thalidomide", Ann. Dermatol Venereol, vol. 10, No. 8, pp. 611-614 (1983).

Naafs, B., Bangkok Workshop on Leprosy Research. Treatment of Reactions and Nerve Damage. Int. J. Lepr. Other Mycobact. Dis., vol. 64, No. 4, Suppl. S21-28 (1996).

Nicolas, J., et al., "Interferon Alfa Therapy in Severe Unresponsive Subacute Cutaneous Lupus Erythematosus", New Engl. J. Med., vol. 321, No. 22, pp. 1550-1551 (1989).

Nicolau, et al., "Thalidomide: Treatment of Severe Recurrent Aphthous Stomatitis in Patients with AIDS", DICP, vol. 24, No. 11, pp. 1054-1056 (1990).

Nielsen, et al., "Thalidomide Enhances Superoxide Anion Release from Human Polymorphonuclear and Leukocytes", Acta. Pathol. Microbiol. Immunol. Scand. [C], vol. 94, No. 6, pp. 233-237 (1986).

Orzalesi, M., "Il Danno Iatrogeno in Neonatologica", Ped. Med. Chir., vol. 14, pp. 105-112 (1992).

Ostraat, et al., "Thalidomide Prolongs Graft Survival in Rat Cardiac Transplants", Transplant Proc., vol. 24, No. 6, pp. 2624-2625 (1992).

Paller, et al., "Proceedings of the Concurrent Sessions", Pediatr. Dermatol, vol. 9, No. 4, pp. 397-406 (1992).

Pearson, et al., "Treatment of Moderately Severe Erythema Nodosum Leprosum with Thalidomide—A Double-Blind Controlled Trial", Lepr. Rev., vol. 40, No. 2, pp. 111-116 (1969).

Pfordte, "Uber die Beeinflussung des Serumproperdinsystems Durch Verschiedene Arzneimittel", Pharmazie, vol. 26, pp. 301-302 (1971).

Phillips, et al., "Tumor Necrosis Factor Aipha (rhTNF) Fails to Stimulate Angiogenesis in the Rabbit Cornea", Anatomical Rec., vol. 245, pp. 53-56 (1996).

Radeff, et al., "Recurrent Aphthous Ulcer in Patient Infected with Human Immunodeficiency Virus: Successful Treatment with Thalidomide", J. Am. Acad. Dermatol, vol. 23, No. 3, Pt. 1, pp. 523-525 (1990).

Rajan, et al., "A Clinical Study of Thalidomide Comparing Pre-Treatment and Post-Treatment Reactional Episodes and Corticosteroid Requirements", Lepr. India, vol. 55, No. 1, 111-116 (1983).

Randall, T., "Investigational New Drug (US) 'Orphan' Trials now Use Thalidomide from two Sources", JAMA, vol. 263, No. 11, p. 1474 (1990).

Roe, et al., "Tumour-Incidence in Progeny of Thalidomide-Treated Mice", British J. Cancer, pp. 331-333, (1965).

Ruggenini, et al., "Talidomide e Tumori Sperimentali", Cancro, vol. 20, pp. 39-55 (1967).

Rustin, et al., "Pyoderma Gangrenosum Associated with Behcet's Disease: Treatment with Thalidomide", J. Am. Acad. Dermatol, vol. 23, No. 5, Pt. 1, pp. 941-944 (1990).

Ryan, et al., "Thalidomide to Treat Esophageal Ulcer in AIDS (6)", New Engl. J. Med., vol. 327, No. 3, pp. 208-209 (1992).

Sampaio, et al., "Prolonged Treatment with Recombinant Interferon Gamma Induces Erythema Nodosum Lepromatous Leprosy Patients", J. Exp. Med., vol. 175, No. 6, pp. 1729-1737 (1992).

Sampaio, et al., "Thalidomide Selectively Inhibits Tumor Necrosis Factor Alpha Production by Stimulated Human Monocytes", J. Exp. Med., vol. 173, No. 3, pp. 699-703 (1991).

Santis, H.R., "Aphthous Stomatitis and its Management", Curr. Opin. Dent, vol. 1, No. 6, pp. 763-768 (1991).

Santos, et al., "In Vitro Tumor Necrosis Factor Production by Mononuclear Cells from Lepromatous Leprosy Patients and from Patients with Erythema Nodosumleprosum", Clin. Immunol. Immunopathol., vol. 67, No. 3 I, pp. 199-203 (1993).

Shannon, et al., "Inhibition of de Novo IgM Antibody Synthesis by Thalidomide as a Relevant Mechanism of Action in Leprosy", Scand. J. Immunol., vol. 13, No. 6, pp. 553-562 (1981).

Shannon, et al., "Thalidomide's Effectiveness in Erythema Nodosum Leprosum is Associated with a Decrease in CD4+ Cells in the Peripheral Blood", Lepr. Rev., vol. 63, No. 1, pp. 5-11 (1992).

Sheehan, N. J., "Thalidomide Neurotoxicity and Rheumatoid Arthritis", Arthritis and Rheuma., vol. 29, No. 10, p. 1296 (1986).

Sheskin, J., "The Treatment of Lepra Reaction in Lepromatous Leprosy. Fifteen Years' Experience with Thalidomide", Int. J. Dermatol., vol. 19, No. 6, pp. 318-322 (1980).

Sheskin, et al., "In Vivo Measurements of Iron, Copper and Zinc in the Skin of Prurigo Nodularis Patients Treated with Thalidomide", Dermatologica, vol. 162, No. 2, pp. 86-90 (1981).

Silverman, W.A., "Medical Inflation", Persp. Biol. Med., pp. 617-637 (1980).

Style, A., "Early Diagnosis and Treatment of Leprosy in the United States", American Family Physician, vol. 52, No. 1, 172-178 (1995).

Sugiura, et al., "Effect of Thalidomide on Transplantable Mouse, Rat, and Hamster Tumors", Gann, vol. 55, pp. 57-60 (1964).

Swift, T.R., "Thalidomide in Erythema Nodosum Leprosum", Lancet, vol. 2, No. 835, p. 966 (1973).

Szydlowska, et al., "On the Application of Thalidomide as a Block of Functional Groups of Proteins in Histochemical Investigations", Folia Histo. Cytochem., vol. 16, No. 3, pp. 233-240 (1978).

Tamura, et al., "Combination Thalidomide and Cyclosporine for Cardiac Allograft Rejection. Comparison with Combination Methylprodnisolone and Cyclosporine", Transplantation, vol. 49, No. 1, p. 20-25 (1990).

Theophilus, S., "Treatment with Thalidomide in Steroid Dependency and Neuritis", Lepr. India, vol. 52, No. 3, pp. 423-428 (1980).

Thomas, et al., "Effect of Thalidomide on Liver Regeneration in Rat", Indian J. Exp. Biol., vol. 10, pp. 314-315 (1972).

Thomas, et al., "Lack of Thalidomide Induced Aplasia in Regenerating Tail of Lizard, *Hemidactylus flavivirdis*", Indian J. Exp. Biol., vol. 10, pp. 316-317 (1972).

Trautman, J. R., "Treatment of Hansen's Disease", Cutis, vol. 18, No. 1, 62-65 (1976).

Van den Broek, H., "Treatment of Prurigo Nodularis with Thalidomide", Arch. Dermatol, vol. 116, No. 5, pp. 571-572 (1980).

Vasilescu, et al., "Cercetari Privind Actiunea Talidomidei Asupra Celulelor Cultivate in Vitro", Cerc. Fiziol., vol. 13, No. 4, pp. 293-300 (1968).

Villa, et al., "Antimytotic Effect of Thalidomide and its Metabolites on the Chick Embryo Blood Cells", Haematol. Latina, vol. 6, pp. 217-221 (1963).

Villa, et al., "Cytological Effects of Thalidomide", The Lancet, pp. 725 (1963).

Vogelsang, et al., "Therapy of Chronic Graft-v-Host Disease in a Rat Model", Blood, vol. 74, No. 1, No. 1, pp. 507-511 (1989).

Vogelsang, et al., "Thalidomide Induction of Bone Marrow Transplantation Tolerance", Transplant Proc., vol. 19, No. 1, Pt. 3, pp. 2658-2661 (1987).

Vogelsang, et al., "Treatment and Prevention of Acute Graft-versus-Host Disease with Thalidomide in a Rat Model", Transplantation, vol. 41, No. 5, pp. 644-647 (1986).

Waters, M., "Use of Thalidomide in Leprosy", BMJ, vol. 303, No. 6800, p. 470 (1991).

Waters, M.F., "An Internally-Controlled Double Blind Trial of Thalidomide in Severe Erythema Nodosum Leprosum", Lepro. Rev., vol. 42, No. 1, pp. 26-42 (1971).

Williams, et al., "Thalidomide Hypersensitivity in AIDS", Lancet, vol. 337, pp. 436-437 (1991).

Winkelmann, et al., "Thalidomide Treatment of Prurigo Nodularis", Acta. Derm. Venereol., vol. 64, No. 5, pp. 412-417 (1984).

Wood, et al., "The Potential use of Thalidomide in the Therapy of Graft-versus-Host Disease—A Review of Clinical and Laboratory Information", Leuk. Res., vol. 14, No. 5, pp. 395-399 (1990).

Woodyatt, P.B., "Thalidomide", The Lancet, p. 750. (1962).

Wulff, et al., "Development of Polyneuropathy During Thalidomide Therapy", Br. J. Dermatol., vol. 112, No. 4, pp. 475-480 (1985).

Yazici, et al., "Practical Treatment Recommendations for Pharmacotherapy of Behcet's Syndrome", Drugs, vol. 42, No. 5, pp. 796-804 (1991).

Youle, et al., "Treatment of Resistant Aphthous Ulceration with Thalidomide in Patients Positive for HIV Antibody", BMJ, vol. 298, No. 6671, p. 432 (1989).

Youle, et al., "Thalidomide in Hyperalgic Pharyngeal Ulceration of AIDS", Lancet, vol. 335, No. 8705, p. 1591 (1990).

Young, et al., "Thalidomide Therapy on a Case of Prurigo Nodularis", Ann. Dermatol., vol. 5, No. 2, pp. 117-120 (1993).

Fazal, N. et al., "Effect of blocking TNF-.alpha. on intracellular BCG (Bacillus Calmette Guerin) growth in human monocyte-derived macrophages", FEMS Microbiology Immunology, vol. 105, pp. 337-346 (1992).

Louzir, B. et al., "Erythroleucemie chez un patient ayant une maladie de Behcet et traite au long cours par thalidomide", Annales De Medecine Interne, vol. 143, pp. 479-480, (1992).

Hatfill, S.J., et al., "Induction of Morphological Differentiation in the Human Leukemic Cell Line K562 by Exposure to Thalidomide Metabolites", Leukemia Research, vol. 15, No. 2/3, pp. 129-136 (1991).

"Thalidomide: 20 Years On", The Lancet, vol. II, No. 8245, pp. 510-511 (1981).

Revuz, J., "Actualite du Thalidomide", Annales De Dermatologie, vol. 117, pp. 313-321 (1990).

Vladutiu, A., "Another Chance for Thalidomide?", The Lancet, vol. I, No. 7444, pp. 981-982 (1966).

Fabro, S. et al., "The Metabolism of Thalidomide: Some Biological Effects of Thalidomide and its Metabolites", British Journal of Pharmacology and Chemotherapy, vol. 25, pp. 352-362 (1965).

Fabro, S., "Biochemical Basis of Thalidomide Teratogenicity", The Biochemical Basis of Chemical Teratogenesis, Chapter 5, pp. 159-178 (1981).

Eisenbud, L. et al., "Recurrent aphthous stomatitis of the Behcet's type: Successful treatment with thalidomide", Oral Surgery, Oral Medicine, Oral Pathology, vol. 64, No. 3, pp. 289-292 (1987).

Buckley, C. et al., "Pyoderma Gagrenosum with Severe Pharyngeal Ulceration", Journal of the Royal Society of Medicine, vol. 83, pp. 290-591 (1990).

Barnes, P.F. et al., "Tumor Necrosis Factor Production in Patients with Leprosy", Infection and Immunity, vol. 60, No. 4, pp. 1441-1446 (1992).

Barnhill, R.L. et al., "Studies on the anti-inflammatory properties of thalidomide: Effects on polymorphonuclear leukocytes and monocytes", Journal of the American Academy of Dermatology, vol. 11, No. 5, Part 1, pp. 814-819 (1984).

Dicken, C.H., "Malignant Pyoderma", Journal of the American Academy of Dermatology, vol. 13, No. 6, pp. 1021-1025 (1985).

O'Patey, et al., "Thalidomide et colite ulcereuse dans la maladie de Behcet", Gastroenierol Clinique Biologique, vol. 13, pp. 104-110 (1989).

Naafs, B. et al., "Thalidomide Therapy", International Journal of Dermatology, vol. 24, No. 2, pp. 131-134 (1985).

Blaschke, V.G. et al., "Chromatographische Racemattrennung von Thalidomide and teratogene Wirkung der Enantiomere", Arzneimittel Forschung Drug Research, vol. II, No. 10, 1640-1642 (1979).

Kaplan, G. et al., "TNF.alpha. regulation of HIV1: biology and therapy", Research in Immunology, vol. 145, No. 8-9, pp. 685-690 (1994).

Bazzoli, A.S. et al., "The effects of thalidomide and two analogues on the regenerating forelimb of the newt", Journal of Embryology and Experimental Morphology, vol. 41, pp. 125-135 (1977).

Bernal, J.E. et al., "Cellular Immune Effects of Thalidomide in Actinic Prurigo", International Journal of Dermatology, vol. 31, No. 8, pp. 599-600 (1992).

Rainsford, K.D., "Disease-modifying antirheumatic and immunoregulatory agents", Bailliere's Clinical Rheumatology International Practice and Research, vol. 4, No. 3, pp. 405-433 (1990).

Hamza, M., "Behcet's disease, palmoplantar pustulosis and HLA-B27 treatment with thalidomide", Clinical and Experimental Rheumatology, vol. 8, No. 4, pp. 427 (1990).

Ehrlich, G.E., "Behcet's Disease: Current Concepts", Comprehensive Therapy, vol. 15, No. 1, pp. 27-30 (1989).

Barriere, H., "Sarcoides Cutanees. Traitement par la thalidomide", La Presse Medicale, vol. 15, No. 12, pp. 963 (1983).

Haffner, M.E., "Studies Involving Orphan Products for Treating/Diagnosing Women's Diseases", Food and Drug Law Journal, vol. 48, pp. 205-211 (1993).

Sherman, et al., "Thalidomide: A Twenty-Five Year Perspective", Food Drug Cosmetic Law Journal, vol. 41, pp. 458-466 (1986).

Burrows, N. P., "Diagnosis and Management of Systemic Lupus Erythematosus Thalidomide Modifies Disease", British Medical Journal, vol. 307, No. 6909, pp. 939-940 (Oct. 1993).

Gutierrez-Rodriguez, O. "Thalidomide A Promising New Treatment for Rheumatoid Arthritis", Arthritis and Rheumatism, vol. 27, No. 10, pp. 1118-1121 (Oct. 1984).

Gutierrez-Rodriguez, O. et al., "Treatment of Refractory Rheumatoid Arthritis—The Thalidomide Experience", Journal of Rheumatology, vol. 16, No. 2, pp. 1158-1163 (Feb. 1989).

Williams, K.M., "Enantiomers in Arthritic Disorders", Pharmacology & Therapeutics, vol. 46, No. 2, pp. 273-295 (1990).

De Cock, K. M., "Treatment of Ulcerative Colitis", letter, British Medical Journal, vol. 1, p. 1356 (May 1979).

Larsson, H., Treatment of Severe Colitis in Behcet's Syndrome with Thalidomide (CG-217), Journal of Internal Medicine, vol. 228, No. 4, pp. 405-407 (Oct. 1990) [letter].

Crain, E. et al., "The Effect of Thalidomide on Experimental Autoimmune Myasthenia Gravis", Journal of Autoimmunity, vol. 2, pp. 197-202 (1989).

Gunzler, V. "Thalidomide—A Therapy for the immunological Consequences of HIV Infection?", vol. 30, No. 2, pp. 105-109 (Oct. 1989).

Handley, J. et al., "Chronic Bullous Disease of Childhood and Ulcerative Colitis", Pediatric Dermatology, vol. 10, No. 3, pp. 256-258 (Sep. 1993).

Handley, J. et al., "Chronic Bullous Disease of Childhood and Ulcerative Colitis", Pediatric Dermatology, vol. 127, Supplement 40, pp. 67-68 (Jul. 1992).

Field, E.O. et al., "Effect of Thalidomide on the Graft Versus Host Reaction", Nature A Weekly Journal of Science, vol. 211, No. 5055, p. 1308-1310 (Sep. 1966).

Hellmann, K. et al., "Prolongation of Skin Homograft Survival by Thalidomide", British Medical Journal, vol. II, pp. 687-689 (Sep. 1965).

Heney, D. et al., "Thalidomide Treatment for Chronic Graft-Versus-Host Disease", British Journal of Haematology, vol. 78, pp. 23-27 (1991).

Keenan, R. J. et al., "Immunosuppressive Properties of Thalidomide Inhibition on In Vitro Lymphocyte Proliferation Alone and in Combination with Cyclosporine or FK506.sup.1", Transplantation, vol. 52, No. 5, pp. 908-910 (Nov. 1991).

Lopez, J. et al., "Thalidomide as Therapy for Intestinal Chronic GVHD", Bone Marrow Transplantation, vol. 11, No. 3, pp. 251-252 (1993).

Bahmer, F. A., Therapy of Lymphocytic Infiltration, Der Hautarzt, vol. 43, p. 663 (1992).

Gershbein L. L., "Effect of Various Agents on Liver Regeneration and Walker Tumor Growth in Partially Hepatectomized Rats", Cancer Research, vol. 26 Part 1, pp. 1905-1908 (Sep. 1966).

Roe, F. J. et al., "Thalidomide and Neoplasia", Nature, vol. 200, pp. 1016-1017 (Dec. 1963). . Makonkawkeyoon, S. et al., "Thalidomide Inhibits the Replication of Human Immunodeficiency Virus Type 1", Proceedings of the National Academy of Sciences, vol. 90, No. 13, pp. 5974-5978 (Jul. 1993).

Meza, A.D. et al., "Managing the Gastrointestinal Complications of AIDS", Drug Therapy, vol. 23, No. 11, pp. 74-83 (1993).

Ghigliotti, G. R. et al., "Thalidomide: Treatment of Choice of Aphthous Ulcers in Patients Seropositive for Human Immunodeficiency Virus", Journal of the American Academy of Dermatology, vol. 28, No. 2, Part 1, pp. 271-272 (Feb. 1993).

Grinspan, D., "Significant Response of Oral Aphthosis to Thalidomide Treatment", American Academy of Dermatology, vol. 12, No. 1, Part 1, pp. 85-90 (Jan. 1985).

Kurkcuoglu, N. et al., "Thalidomide in the Treatment of Recurrent Necrotic Mucocutaneious Aphthae", British Journal of Dermatology, vol. 112, No. 5, p. 632 (May 1985).

Powell, R.J. et al., "Investigation and Treatment of Orogenital Ulceration; Studies on a Possible Mode of Action of Thalidomide", British Journal of Dermatology, vol. 113, Supplement 28, pp. 141-144 (1985).

Revuz, J. et al., "Crossover Study of Thalidomide vs. Placebo in Severe Recurrent Aphthous Stomatitis", Archives of Dermatology, vol. 126, No. 7, pp. 923-927 (Jul. 1990).

Apt, W., "Effect of Thalidomide on the Course of Experimental Chagas' Disease", BOI Chili Parasitol, vol. 20, No. 3, pp. 84-86 (Sep. 1965).

Vicente, T. et al., "In Vitro Activity of Thalidomide against mycobacterium Avium Complex", Archives of Internal Medicine, vol. 153, p. 534 (Feb. 1993).

Eravelly, J. et al., "Thalidomide in Weber-Christian Disease", Lancet, vol. 1, No. 8005, p. 251 (1977) [letter].

Lueprasitasakul, W. et al., "Effect of Thalidomide on the incidence of Iodine-Induced and Spontaneous Lymphocytic Thyroiditis and Spontaneous Diabetes Mellitus in the BB/W or Rat", Acta Endocrino Logica, vol. 123, No. 1, pp. 79-83 (Jul. 1990).

Misery, L. et al., "Remission of Langerhans Cell Histiocytosis with Thalidomide Treatment", Clinical and Experimental Dermatology, vol. 18, No. 5, p. 487 (Sep. 1993).

Rhoton, A.J., "Rle for Thalidomide in Primary Biliary Cirrhosis Treatment", Gastroenterology, vol. 105, No. 3, p. 956 (Sep. 1993).

Thomas, L. et al., "Successful treatment of Adult's Langerhans Cell Histiocytosis with Thalidomide, Report of Two cases and Literature Review", Archives of Dermatology, vol. 129, pp. 1261-1264 (Oct. 1993).

Fabro, S. et al., "Teratogenic Activity of Thalidomide and Related Compounds," Life Sciences, 3:987-992 (1964).

Shealy et al., "D- and L-Thalidomide," Chem. And Indus., pp. 1030-1031 (Jun. 12, 1965).

Folkman, "Tumor Angiogenesis: Therapeutic Implications," The New England Journal of Medicine, 285(21):1182-1186 (Nov. 18, 1971).

Jonsson, N. Ake, et al., "Chemical Structure and Teratogenic Properties," Acta Pharm. Succica, 9:521-542 (1972).

Jonsson, N. Ake, et al., "Chemical Structure and Teratogenic Properties," Acta Pharm. Succica, 9:431-446 (1972).

Jonsson, N. Ake, et al., "Chemical Structure and Teratogenic Properties," Acta Pharm. Succica, 9:543-562 (1972).

Eriksson, Sven O., "Synthesis and Alkaline Hydrolysis of some N-substituted Phthalimides," Acta Pharm. Sucecica, 10:63-74 (1973).

Gimbrone et al., "Tumor Growth and Neovascularization: An Experimental Model Using the Rabbit Cornea," J. Nat'l Cancer Institute, 52(2):413-419 (1974).

Fickentscher, K., "Stereochemical Properties and Teratogenic Activity of Some Tetrahydrophthalimides," Mol. Pharmacology, 13:133-141 (1977).

Knighton et el., "Avascular and Vascular Phases Of Tumor Growth In The Chick Embryo," Br. J. Cancer, 35:347-356 (1977).

Blaschke, "Chromatographic Separation of Racemic Thalidomide and Teratogenic Activity of its Enantiomers (Chromatographische Racemattrennung von Thalidomid und teratogene Wirkung der Enantiomere)," Drug Research, 29 (II/10): 1640-1642 (1979). (English lang. summary on first page).

Muthukkaruppan et al., "Angiogenesis in the Mouse Cornea," Science, 205:1416-1418 (Sep. 28, 1979).

Waters, et al., "Treatment of Ulcerative Colitis with Thalidomide," British Medical Journal, p. 792 (Mar. 24, 1979).

Flohe et al., "Studies on the Hypothetical Relationship of Thalidomide-induced Embryopathy and Collagen Biosynthesis," Arzneimittelforschung (Germany, West), 31(2):315-20 (1981).

Helm, Drug Research, 31 (I/6): 941-949 (1981).

Taylor et al., Nature, 297: p. 307 (1982).

Belaube et al., "Should Thalidomide be Rehabilitated?," Sem. Hop. Paris, 59(45):3101-3104 (Dec. 8, 1983).

Folkman et al., Science, 221: p. 719 (1983).

Hendler, Sheldon S. et al., "Thalidomide for Autoimmune Disease," Medical Hypotheses, 10:437-443 (1983).

Crum et al., Science, 230: 1375 et seq. (1985).

Sidky et al., Cancer Research, 47: pp. 5155-5161 (1987).

Srivastava et al., "The Prognostic Significance of Tumor Vascularity in Internediate-Thickness Skin Melanoma," Am. J. Pathol., 133:419-423 (1988). (abstract from Medline: Accession No. 06745734).

Chen et al., "Plasam Pharmacokinetics and Urinary Excretion of Thalidomide After Oral Dosing in Healthy Male Volunteers," Drug Metabolism and Disposition, 17(4):402-405 (1989).

White et al., New England J. Med., 320: pp. 1197-1200 (1989).

Folkman et al., "Induction of Angiogenesis During the Transition from Hyperplasia to Neoplasia," Nature, 339:58-61 (May 4, 1989).

"Thalidomide," The Merck Index, Eleventh Edition, Budavari et al., eds., Merck & Co., New Jersey, p. 9182 (1989).

Eger, K. et al., "Synthesis, Central Nervous System Activity and Teratogenicity of a Homothalidomide," Arzneim.-Forsch/Drug Res. 40 (II. Nr. 10):1073-1075 (1990).

Ingber et al., "Synthetic Analogs of Fumagillin That Inhibit Angiogenesis and Supress Tomour Growth," Nature, 348:555-557 (Dec. 6, 1990).

Brem et al., Neurosurg., 74: 441-446 (1991).

Matsuyama, Toshifumi, "Cytokines and HIV infection: is AIDS a Tumor Necrosis Factor Disease?," AIDS, 5(12):1405-1417 (1991).

Weidner et al., "Tumor Angiogenesis and Metastasis—Correlation in Invasive Breast Carcinoma," N. E. J. Med., 324(1):1-8 (1991).

Colville-Nash et al., "Angiogenesis and Rheumaoid Arthritis: Pathogenic and Therapeutic Implications," Ann. Rheum. Dis., 51:919-925 (1992).

Folkman and Shing, "Angiogenesis," J. Biol. Chem., 267(16):10931-10934 (1992).

Schweigerer and Fotsis, "Angiogenesis and angiogenesis inhibitors in paediatric diseases," Eur. J. Pediatr. 151:472-476 (1992).

Torry and Rongish, Angiogenesis in the Uterus: Potential Regulation and Relation to Tumor Angiogenesis, Am. J. Reprod. Immunol., 27:171-179 (1992).

Vogelsang et al., "Thalidomide for the Treatment of Chronic Graft-Versus-Host Disease," New England Journal of Medicine, 326:1055-1058 (1992).

Weidner et al., "Angiogenesis in Prostate Carcinoma," Am. J. Path., 143(2):401-409 (1993).

D'Amato et al., "Thalidomide is an Inhibitor Angiogenesis," PNAS USA, 91:4082-4085 (1994).

Oikawa et al., "Eponemycin, A Novel Antibiotic, is a Highly Powerful Angiogenesis Inhibitor," Biochem. Biophys. Res. Comm., 181(3):1070-1076 (Dec. 31, 1991).

Otsuka et al., "A New Potent Angiogenesis Inhibitor, FR-118487," J. Microb. Biotech., 1(3):163-168 (1991).

Sausville et al., "Contributions of humor tumor xenografts to anticancer drug development," Cancer Research, 2006, 66:3351-3354.

Johnson et al., "Relationships between drug activity in NCI preclinical in vitro and in vivo models and early clinical trials," British J. of Cancer, 2001, 84(10):1424-1431.

Ace Animals, Inc., www.aceanimals.com/SpragueDawley.htm, 2004, pp. 1-3.

Medline AN 93246378, Kantorowitz et al., International J. Radiation Oncol., Biol., Physics, Apr. 30, 1993, 26(1):89-94, abstract.

Medline AN 91105904, Thompson et al., Carcinogenesis, Jan. 1991, 12(1):111-114, abstract.

Medline AN 88225378, Hershman et al., Eu. J Surgical Oncology, Jun. 1988, 14(3):249-251, abstract.

Biosis AN 1990:450534, Rogers et al., Nutrition Res., 1990, 10(8):915-928, abstract.

Biosis AN 1990:220159, Lino et al., Oncology, 1990, 47(2):185-190, abstract.

Furman, R.R., "Thalidomide alone or in combination with fludarbabine are effective treatments for patients with fludarabine-relapsed and refractory CLL", American Society of Clinical Oncology, May 2005, Abstract #6640.

Furman, Richard, et al., "Thalidomide is active alone and in combination with fludarabine in fludarabine-relapsed and refractory chronic lymphocytic leukemia", Dec. 2004, Abstract #4835.

Furman, Richard, "Thalidomide With or Without Fludarabine in Treating Patients with Hematologic Cancer", ClinicalTrials.gov on Dec. 31, 2007.

Steins, Martin, et al., "Efficacy and safety of thalidomide in patients with acute myeloid leukemia", Blood, Feb. 2002, 99(3):834-839.

Steins, M.B., et al., "Thalidomide for the Treatment of Acute Myeloid Leukemia", Leukemia & Lymphoma, Sep. 2003, 44(9):1489-1493.

Kreuter, Michael, et al., "Downregulation of neuropilin-1 in patients with acute myeloid leukemia treated with thalidomide", European Journal of Haemotology, 2007, 79:392-397.

Strupp, C., et al., "Hairy cell leukemia (HCL) with extensive myelofibrosis responds to thalidomide", Leukemia Research, 2005, 29:967-969.

Wöhrer, Stefan, et al., "Effective treatment of primary plasma cell leukemia with thalidomide and dexamethasone—a case report", The Hematology Journal, 2004, 5:361-363.

Ruan, Jia, et al., "Targeting angiogenesis in mantle cell lymphoma: Clinical efficacy and correlative studies of a phase II trial of RT-PEPC (rituximab, thalidomide and metronomic oral chemotherapy with prednisone, etoposide, procarbazine and cyclophosphamide) in relapsed/refractory disease)", American Society of Hematology, Dec. 2006, Abstract #2751.

Damaj, G, et al., "Thalidomide therapy induces response in relapsed mantle cell lymphoma", Leukemia, 2003, 17:1914-1915.

Goy, Andre, "New Directions in the Treatment of Mantle Cell Lymphoma: An Overview", Clinical Lymphoma & Myeloma, Oct. 2006, 7(Supp 1):S24-S32.

Game, Melaku, et al., "Thalidomide and low dose Vinblastine as palliative therapy for patients relapsing after autotransplant for Hodgkin's Disease (HD) and Non-Hodgkin's Lymphoma (NHL)", American Society of Hematology, Dec. 2001, Abstract #5235.

Larson, Melissa, et al., "HIV-related Lymphoma Treated with Maintenance Thalidomide", Clinical Advances in Hematology & Oncology, Mar. 2005, 3(3):231-235.

Ramasamy, Karthik, et al., "Successful treatment of refractory angioimmunoblastic T-cell lymphoma with thalidomide and dexamethasone", Haematologica, 2006, 91(1):117-118.

Folkman, Judah, "Angiogenesis: an organizing principle for drug discovery?", Nature Reviews, Apr. 2007, 6:273-286.

Thomas, Deborah, et al., "Current role of thalidomide in cancer treatment," Current Opinion in Oncology, 2000, 12:564-573.

Brennen, W. Nathaniel, et al., "Thalidomide and Analogues: Current Proposed Mechanisms and Therapeutic Usage," Clinical Prostate Cancer, Jun. 2004, 54-61.

May 22, 2008 letter from Sterne, Kessler, Goldstein & Fox regarding Supplemental Notification Pursuant to § 505(j)(2)(B)(ii) of the Federal Food, Drug, and Cosmetic Act.

Jurand, A., "Early changes in limb buds of chick embryos after thalidomide treatment," J. Embryol. Exp. Morph., Oct. 1966, 16(2):289-300.

Gimbrone Jr., Michael A., "Tumor Dormancy in Vivo by Prevention of Neovascularization," The Journal of Experimental Medicine, 1972, 136:261-276.

Rajkumar, S. Vincent, "Thalidomide in Multiple Myeloma," Oncology, 2000, Supplement 13:11-16.

Ribatti, et al., "Is thalidomide a true anti-angiogenic molecule in multiple myeloma," Haemotologica, 2002, 84(4):344-345.

Ribatti, et al., "On the use of thalidomide as an antiangiogenic agent in the treatment of multiple myeloma," Ann. Hematol., 2003, 82:262.

Rinaldi, "Thalidomide and Morphogenetic Processes in the Adult. Effect of Thalidomide on the Regeneration of the Tail Triturus Cristatus," Boll. Soc. Ital. Biol., 1969, 45(13):1268-1272.

Hatjiharissi, et al., "The Combination of Intermediate Doses of Thalidomide and Dexamethasone Reduces Bone Marrow Micro-Vessel Density But Not Serum Levels of Angiogenic Cytokines in Patients with Refractory/Relapsed Multiple Myeloma," Hematological Oncology, 2004, 22(4):159-68.

Rajkumar, et al., "Thalidomide in the Treatment of Plasma Cell Malignancies," Journal of Clinical Oncology, 2001, 19(16):3593-3595.

Bruno, et al., "New drugs for treatment of multiple myeloma," The Lancet Oncology, 2004, 5(7):430-442.

Kerbel, et al., "Clinical Translation of Angiogenesis Inhibitors," Nature Reviews Cancer, 2002, 2:727-739.

Eleutherakis-Papaiakovou, et al., "Bone Marrow Angiogenesis and Progression in Multiple Myeloma: Clinical Significance and Therapeutic Approach," Leukemia and Lymphoma, 2003, 44(6):937-948.

Richardson, et al., "Thalidomide: Emerging Role in Cancer Medicine," Annu. Rev. Med., 2002, 53:629-657.

Kumar, et al., "Effect of thalidomide therapy on bone marrow angiogenesis in multiple myeloma," Leukemia, 2004, 1-4.

Vacca, et al., "Thalidomide Downregulates Angiogenic Genes in Bone Marrow Endothelial Cells of Patients with Active Multiple Myeloma," Journal of Clinical Oncology, 2005, 22(23):5334-5346.

Braun, A.G. et al., "Teratogen Metabolism," Energy Research Abstracts, U.S. Department of Energy, Technical Information Center Office of Scientific & Technical Information, (1984) 9(8):5508:15072.

Braun, A.G. et al., "Teratogen Metabolism: Activation of Thalidomide and Thalidomide Analogues to Products that Inhibit the Attachment of Cells to Concanavalin A Coated Plastic Surfaces," Energy Research Abstracts, U.S. Department of Energy, Technical Information Center Office of Scientific & Technical Information, (1984) 9(8):5508:15071.

Braun, A.G. et al., "Teratogen Metabolism : Activation of Thalidomide and Thalidomide Analogues to Products that Inhibit the Attachment of Cells to Concanavalin a Coated Plastic Surfaces," Biochemical Pharmacology (1984) 33(9):1471-1477.

Braun, A.G. et al., "Teratogen Metabolism : Activation of Thalidomide and Thalidomide Analogues to Products that Inhibit the Attachment of Cells to Concanavalin a Coated Plastic Surfaces," Revised Version, U.S. Department of Commerce, National Technical Information Services, Harvard Medical School: Boston, MA (1982) DE84006118.

Gordon, G. "Mutagenic and Cytotoxic Studies with Thalidomide," (unpublished Ph.D. dissertation, The John Hopkins U. 1981) (microformed on UMI Dissertation Abstracts database 8120023).

Gordon, G.B. et al., "Thalidomide Teratogenesis: Evidence for a Toxic Arene Oxide Metabolite," Federation of American Societies for Experimental Biology Federation Proceedings (1981) 40(3):2508.

Gordon, G.B. et al., "Thalidomide Teratogenesis: Evidence for a Toxic Arene Oxide Metabolite," Proc. Natl. Acad. Sci. (1981) 78(4):2545-2548.

Lisek, C.A. "Structural Elucidation of a Hydroxylated Metabolite of Thalidomide: Evidence Supporting an Arene Oxide Intermediate," (unpublished Ph.D. dissertation, The John Hopkins U. 1985) (microformed on UMI Dissertation Abstracts database 8609337).

Barlogie, et al., "Duration of Survival in Patients with Myeloma Treated with Thalidomide," The New England Journal of Medicine, Jul. 10, 2008, 210-212.

Zangari, et al., "Eight-year median survival in multiple myeloma after total therapy 2: roles of thalidomide and consolidation chemotherapy in the context of total therapy 1," British Journal of Haematology, 2008, 141:433-444.

Simmons, et al., "Induction of the hepatic mixed-function oxidase system by synthetic glucocorticoids," The Journal of Biological Chemistry, 1987, 262(1):326-332.

Kim, et al., "In vivo radioprotective effects of oltipraz in gamma-irradiated mice," Biochem Pharmacol, May 1998, 55(10):1585-90, Abstract.

Bell, et al., "Glucocorticoid repression and basal regulation of the epoxide hydrolase promoter," Arch Biochem Biophys., Jun. 1990, 279(2):363-9, Abstract.

Ferrari, et al., "Differential effects of human recombinant interleukin-1 beta and dexamethasone on hepatic drug-metabolizing enzymes in male and female rats," Biochem Pharmacol., Jun. 1993, 45(11):2269-77, Abstract.

Nam, et al., "Correlation of increased mortality with the suppression of radiation-inducible microsomal epoxide hydrolase and glutathione S-transferase gene expression by dexamethasone: effects on vitamin C and E-induced radioprotection," Biochem-Pharmacol., Nov. 1998, 56(10):1295-304, Abstract.

Avalos-Diaz, et al., "Inhibitory Effect on Endocytosis in Polymorphonuclear Cells Caused by Thalidomide", Arch. Invest. Med., vol. 16, No. 2, pp. 139-143 (1985).

Dhodapkar, et al., "A Phase II Pilot Study of Anti-Angiogenesis Therapy Using Thalidomide in Patients with Multiple Myeloma", UARK 98-003, pp. 1-15 (1998).

Gaetani, M., "Studi Sull'Attivita Antitumorale Della Talidomide", Giomale Italiano diu Chemioterapia, pp. 83-86 (1964).

Kenyon, et al., "The Discovery of New Inhibitors of Angiogenesis Using an Improved Mouse Corneal Neovascularization Model", No. 459-367, p. S94 (Abstract only) (1994).

Neubert, "Teratogenicity: Any Relationship to Carcinogenicity?", Institute for Toxicology and Embryopharmacology, Free University of Berlin, Berlin, Federal Rep. Of Germany, pp. 169-178 (1979).

Peyron, et al., "The Pharmacological Basis for the Treatment of Photodermatoses", Biochimie, vol. 68, No. 6, pp. 899-904 (1986).

Proenca, N.G., "Thalidomide: An Eclectic Medication in Dermatology", Rev. Paul. Med., vol. 107, No. 1, pp. 41-46 (1989).

Smith, et al., "Studies on the Relationship Between the Chemical Structure and Embryotoxic Activity of Thalidomide and Related Compounds", Chemical Structure and Embryopathy, pp. 194-209 (1965).

Wesolowski, et al., "Effect of Light on a Murine Model of Retinopathy of Prematurity", Invest. Opthamol. & Visual Science, vol. 33, No. 4, p. 1281 (Abstract only) (1992).

Aug. 13, 2008. Defendant Barr Laboratories. Inc.'s Answer, Counterclaims and Demand for Jury Trial, *Celgene Corporation v. Barr Laboratories, Inc.*, Civil Action No. 07-286 (SDW)(MCA).

E. Genoveti. "Effeti Della Somministrazione Di Talidomide Sugli Eteroinnesti Coreali," *Nota I—Arch. E Atti Soc. Med. Chim Messina*, 1965, XI(3):377-382.

Gilani, S.H., "Cardiovascular Malformations in the Chick Embryo Induced by Thalidomide," *Toxicology and Applied Pharmacology*, 1973, 25(1):77-83.

Smith, A. and Wolpert, L., "Nerves and angiogenesis in amphibian limb regeneration," *Nature*, 1975, 257:224-225.

Rageh, M. et al., "Vasculture in Pre-Blastema and Nerve-Dependent Blastema Stages of Regenerating Forelimbs of the Adult Newt, *Notophthalmus viridescens*," *Journal of Experimental Zoology*, 2002, 292:255-266.

Cordingley, F. et al., "Tumour Necrosis Factor as an Autocrine Tumour Growth Factor for Chronic B-Cell Malignancies," *The Lancet*, Apr. 30, 1988, 969-971.

Brent, R. and Holmes, L., "Clinical and Basic Science Lessons from the Thalidomide Tragedy: What Have We Learned About the Causes of Limb Defects?", *Teratology*, 1988, 38:241-251.

De, A. and Pal, D., "Quantitative Structure-Activity Relationship (QSAR) and Rational Drug Design for Some Antineoplastic Thalidomide and Glutarimide Derivatives," *J. Indian Chem. Soc.*, 1976, LIII:1049-1052.

De A. and Pal, D., "Possible Antineoplastic Agents II," *Journal of Pharmaceutical Sciences*, 1977, 66(2):232-235.

Gilani, S., "Cardiovascular Malformations in the Chick Embryo Induced by Thalidomide," *Toxicology and Applied Pharmacology*, 1973, 25:77-83.

"Thalidomide—a possible alternative as an immune-modulating drug," *Lakartidningen*, 1989, 86(48):4260-4262.

Missirlis, E. et al., "Angiogenesis is Associated with Collagenous Protein Synthesis and Degradation in the Chick Chorioallantoic Membrane," *Tissue and Cell*, 1990, 22(4):419-426.

Tsutsumi, S. and Gidoh, M., "Inefficacy of Thalidomide on Rat Adjuvant-induced Arthritis and Lack of Arthrogenecity of Hansen Bacilli," *Jap. J. Leprosy*, 1988, 57:122-128.

Wolpert, L., "Mechanisms of Limb Development and Malformation," *Br. Med. Bull.*, 1976, 32(1):65-70.

Invalidation Petition of KR 506043 dated Apr. 6, 2009 and Supplemental Brief dated Oct. 29, 2009.

Folkman, J. and Klagsburn, M., "A family of angiogenic peptides," *Nature*, 1987, 329:671-672.

Leibovich, S. et al., "Macrophage-induced angiogenesis is mediated by tumour necrosis factor-$\alpha$," *Nature*, 1978, 329:630-632.

Korean Patent Infringement Decision in 506043 dated Dec. 21, 2009.

Interlocutory Decision of Opposition to EP Patent No. 1 264 597 dated Nov. 9, 2009.

Communication in corresponding Canadian Patent Application No. 2,514,681 dated Jan. 5, 2009.

Alexanian, Raymond et al., "Thalidomide for Resistant and Relapsing Myeloma," *Seminars in Hematology*, 2000, 37(1)Supp 3:22-25.

Bertolini, F. et al., "Thalidomide in multiple myeloma, myelodysplastic syndromes and histiocytosis. Analysis of clinical results and of surrogate angiogenesis markers," *Annals of Oncology*, 2001, 12:987-990.

Cavenaugh, Jamie D., "Thalidomide in Multiple Myeloma: Current Status and Future Prospects," *British Journal of Haematology*, 2003, 120:18-26 .

D'Amato, Robert et al., "Mechanism of Action of Thalidomide and 3-Aminothalidomide in Multiple Myeloma," *Seminars in Oncology*, 2001, 28(6): 597-601.

Juliusson, Gunnar et al., "Frequent good partial remissions from thalidomide including best response ever in patients with advanced refractory and relapsed myeloma," *British Journal of Haemotology*, 2000, 109:89-96.

Kakimoto, T. et al., "Thalidomide for the Treatment of Refractory Multiple Myeloma: Association of Plasma Concentrations of Thalidomide and Angiogenic Growth Factors with Clinical Outcome,"*Jpn. J. Cancer Res.*, 2002, 93:1029-1036.

Kneller, A. et al., "Therapy with thalidomide in refractory multiple myeloma patients—the revival of an old drug," *British Journal of Haematology*, 2000, 108:391-393.

Kumar, S. et al., "Effect of thalidomide therapy on bone marrow angiogenesis in multiple myeloma," *Leukemia*, 2004, 1-4.

Kumar, S. et al., "Thalidomide as an anti-cancer agent," *J. Cell. Mol. Med.*, 2002, 6(2):160-174.

Peuckmann, Vera et al., "Potential Novel Uses of Thalidomide," *Drugs*. 2000, 60(2):273-292.

Raje, Noopur et al., "Thalidomide and immunology drugs as cancer therapy," *Current Opinions in Oncology*. 2002, 14:635-640.

Rajkumar, S.V. et al., "Thalidomide for previously untreated indolent or smoldering multiple myelorna," *Leukemia*, 2001, 15:1274-1276.

Rajkumar, S.V. et al., "Thalidomide in the Treatment of Relapsed Multiple Myeloma," *Mayo Clin Proc.*, 2000, 75:897-901.

Rajkumar, S.V., "Thalidomide in the treatment of multiple myeloma," *Expert Rev. Anticancer Ther.*, 2001, 1(1):20-28.

Ribatti, D. et al., "Is thalidomide a true anti-angiogenic molecule in multiple myeloma?" *Haematologica*, 2002, 87(4):344-345.

Richardson, Paul et al., "Thalidomide: Emerging Role in Cancer Medicine," *Annu. Rev. Med.*, 2002, 53:629-657.

Roe, F.J.C., "Research on Anticarcinogenic Effects of Thalidomide," *The Practitioner*, 1974, 212(1269):296-297.

Tosi, Patrizia et al., "Thalidomide in multiple myeloma: state of art" *Haematologica*, 2002, 87(3):233-234.

Vacca, A. et al., "Bone marrow angiogenesis and progression in multiple myeloma," *British Journal of Haematology*, 1994, 87:503-508.

* cited by examiner

METHODS FOR INHIBITING UNDESIRED ANGIOGENESIS IN PATIENTS HAVING TUMORS WITH THALIDOMIDE

CROSS-REFERENCE TO RELATED APPLICATION

This application is a divisional application of U.S. patent application Ser. No. 09/704,054, filed Nov. 1, 2000, which is a divisional of Ser. No. 09/545,139, filed Apr. 7, 2000, now U.S. Pat. No. 6,469,045, which is a divisional of Ser. No. 08/950,673, filed Oct. 16, 1997, now U.S. Pat. No. 6,071,948, which is a continuation of Ser. No. 08/468,792, filed Jun. 6, 1995, now U.S. Pat. No. 5,712,291, which is a continuation of Ser. No. 08/168,817, filed Dec. 15, 1993, now U.S. Pat. No. 5,629,327, which is a continuation-in-part of U.S. patent application Ser. No. 08/025,046 filed Mar. 1, 1993, now abandoned, the disclosure of each of which is incorporated herein by reference in its entirety.

TECHNICAL FIELD

The present invention relates to methods and compositions for preventing unwanted angiogenesis in a human or animal. More particularly, the present invention relates to a method for preventing unwanted angiogenesis, particularly in angiogenesis dependent or associated diseases, by administration of compounds such as thalidomide and related compounds.

BACKGROUND OF THE INVENTION

As used herein, the term "angiogenesis" means the generation of new blood vessels into a tissue or organ. Under normal physiological conditions, humans or animals only undergo angiogenesis in very specific restricted situations. For example, angiogenesis is normally observed in wound healing, fetal and embryonal development and formation of the corpus luteum, endometrium and placenta. The control of angiogenesis is a highly regulated system of angiogenic stimulators and inhibitors. The control of angiogenesis has been found to be altered in certain disease states and, in many cases, the pathological damage associated with the disease is related to the uncontrolled angiogenesis.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel. In the disease state, prevention of angiogenesis could avert the damage caused by the invasion of the new microvascular system.

Persistent, unregulated angiogenesis occurs in a multiplicity of disease states, tumor metastasis and abnormal growth by endothelial cells and supports the pathological damage seen in these conditions. The diverse pathological states created due to unregulated angiogenesis have been grouped together as angiogenic dependent or angiogenic associated diseases. Therapies directed at control of the angiogenic processes could lead to the abrogation or mitigation of these diseases.

One example of a disease mediated by angiogenesis is ocular neovascular disease. This disease is characterized by invasion of new blood vessels into the structures of the eye such as the retina or cornea. It is the most common cause of blindness and is involved in approximately twenty eye diseases. In age-related macular degeneration, the associated visual problems are caused by an ingrowth of chorioidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasia. Other diseases associated with corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes oster infections, protozoan infections, Kaposi sarcoma, Mooren ulcer, Terrien's marginal degeneration, mariginal keratolysis, rheumatoid arthritis, systemic lupus, polyarteritis, trauma, Wegeners sarcoidosis, Scieritis, Steven's Johnson disease, periphigoid radial keratotomy, and corneal graph rejection.

Diseases associated with retinal/choroidal neovascularization include, but are not limited to, diabetic retinopathy, macular degeneration, sickle cell anemia, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications. Other diseases include, but are not limited to, diseases associated with rubeosis (neovasculariation of the angle) and diseases caused by the abnormal proliferation of fibrovascular or fibrous tissue including all forms of proliferative vitreoretinopathy.

Another disease in which angiogenesis is believed to be involved is rheumatoid arthritis. The blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Factors associated with angiogenesis may also have a role in osteoarthritis. The activation of the chondrocytes by angiogenic-related factors contributes to the destruction of the joint. At a later stage, the angiogenic factors would promote new bone formation. Therapeutic intervention that prevents the bone destruction could halt the progress of the disease and provide relief for persons suffering with arthritis.

Chronic inflammation may also involve pathological angiogenesis. Such disease states as ulcerative colitis and Crohn's disease show histological changes with the ingrowth of new blood vessels into the inflamed tissues. Bartonellosis, a bacterial infection found in South America, can result in a chronic stage that is characterized by proliferation of vascular endothelial cells. Another pathological role associated with angiogenesis is found in atherosclerosis. The plaques formed within the lumen of blood vessels have been shown to have angiogenic stimulatory activity.

One of the most frequent angiogenic diseases of childhood is the hemangioma. In most cases, the tumors are benign and regress without intervention. In more severe cases, the tumors progress to large cavernous and infiltrative forms and create clinical complications. Systemic forms of hemangiomas, the hemangiomatoses, have a high mortality rate. Therapy-resistant hemangiomas exist that cannot be treated with therapeutics currently in use.

Angiogenesis is also responsible for damage found in hereditary diseases such as Osler-Weber-Rendu disease, or hereditary hemorrhagic telangiectasia. This is an inherited disease characterized by multiple small angiomas, tumors of blood or lymph vessels. The angiomas are found in the skin and mucous membranes, often accompanied by epistaxis (nosebleeds) or gastrointestinal bleeding and sometimes with pulmonary or hepatic arteriovenous fistula.

Angiogenesis is prominent in solid tumor formation and metastasis. Angiogenic factors have been found associated with several solid tumors such as rhabdomyosarcomas, retinoblastoma, Ewing sarcoma, neuroblastoma, and osteosarcoma. A tumor cannot expand without a blood supply to provide nutrients and remove cellular wastes. Tumors in which angiogenesis is important include solid tumors, and benign tumors such as acoustic neuroma, neurofibroma, trachoma and pyogenic granulomas. Prevention of angiogenesis could halt the growth of these tumors and the resultant damage to the animal due to the presence of the tumor.

It should be noted that angiogenesis has been associated with blood-born tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen. It is believed that angiogenesis plays a role in the abnormalities in the bone marrow that give rise to leukemia-like tumors.

Angiogenesis is important in two stages of tumor metastasis. The first stage where angiogenesis stimulation is important is in the vascularization of the tumor which allows tumor cells to enter the blood stream and to circulate throughout the body. After the tumor cells have left the primary site, and have settled into the secondary, metastasis site, angiogenesis must occur before the new tumor can grow and expand. Therefore, prevention of angiogenesis could lead to the prevention of metastasis of tumors and possibly contain the neoplastic growth at the primary site.

Knowledge of the role of angiogenesis in the maintenance and metastasis of tumors has led to a prognostic indicator for breast cancer. The amount of neovascularization found in the primary tumor was determined by counting the microvessel density in the area of the most intense neovascularization in invasive breast carcinoma. A high level of microvessel density was found to correlate with tumor recurrence. Control of angiogenesis by therapeutic means could possibly lead to cessation of the recurrence of the tumors.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula.

In wound healing, excessive repair or fibroplasia can be a detrimental side effect of surgical procedures and may be caused or exacerbated by angiogenesis. Adhesions are a frequent complication of surgery and lead to problems such as small bowel obstruction.

Several kinds of compounds have been used to prevent angiogenesis. Taylor et al. have used protamine to inhibit angiogenesis, see Taylor et al., *Nature* 297:307 (1982). The toxicity of protamine limits its practical use as a therapeutic. Folkman et al. have disclosed the use of heparin and steroids to control angiogenesis. See Folkman et al., *Science* 221:719 (1983) and U.S. Pat. Nos. 5,001,116 and 4,994,443. Steroids, such as tetrahydrocortisol, which lack gluco and mineral corticoid activity, have been found to be angiogenic inhibitors.

Other factors found endogenously in animals, such as a 4 kDa glycoprotein from bovine vitreous humor and a cartilage derived factor, have been used to inhibit angiogenesis. Cellular factors such as interferon inhibit angiogenesis. For example, interferon $\alpha$ or human interferon $\beta$ has been shown to inhibit tumor-induced angiogenesis in mouse dermis stimulated by human neoplastic cells. Interferon $\beta$ is also a potent inhibitor of angiogenesis induced by allogeneic spleen cells. See Sidky et al., *Cancer Research* 47:5155-5161 (1987). Human recombinant $\alpha$ interferon (alpha/A) was reported to be successfully used in the treatment of pulmonary hemangiomatosis, an angiogenesis-induced disease. See White et al., *New England J. Med.* 320:1197-1200 (1989).

Other agents which have been used to inhibit angiogenesis include ascorbic acid ethers and related compounds. See Japanese Kokai Tokkyo Koho No. 58-131978. Sulfated polysaccharide DS 4152 also shows angiogenic inhibition. See Japanese Kokai Tokkyo Koho No. 63-119500. A fungal product, fumagillin, is a potent angiostatic agent in vitro. The compound is toxic in vivo, but a synthetic derivative, AGM 12470, has been used in vivo to treat collagen II arthritis. Fumagillin and O-substituted fumagillin derivatives are disclosed in EPO Publication Nos. 0325199A2 and 0357061A1.

PCT Application No. WO 92/14455 to Kaplan et al. is directed to a method for controlling abnormal concentration of TNF-$\alpha$ by administering thalidomide or thalidomide derivatives to a patient with toxic concentrations of TNF-$\alpha$.

The above compounds are either topical or injectable therapeutics. Therefore, there are drawbacks to their use as a general angiogenic inhibitor and lack adequate potency. For example, in prevention of excessive wound healing, surgery on internal body organs involves incisions in various structures contained within the body cavities. These wounds are not accessible to local applications of angiogenic inhibitors. Local delivery systems also involve frequent dressings which are impracticable for internal wounds, and increase the risk of infection or damage to delicate granulation tissue for surface wounds.

Thus, a method and composition are needed that are capable of inhibiting angiogenesis and which are easily administered. A simple and efficacious method of treatment would be through the oral route. If an angiogenic inhibitor could be given by an oral route, the many kinds of diseases discussed above, and other angiogenic dependent pathologies, could be treated easily. The optimal dosage could be distributed in a form that the patient could self-administer.

SUMMARY OF THE INVENTION

In accordance with the present invention, compositions and methods are provided that are effective in inhibiting unwanted angiogenesis. These compositions are easily administered by different routes including oral and can be given in dosages that are safe and provide angiogenic inhibition at internal sites. The present invention provides a method of treating mammalian diseases mediated by undesired and uncontrolled angiogenesis by administering a composition comprising an anti-angiogenic compound in a dosage sufficient to inhibit angiogenesis.

The present invention also includes angiogenic inhibiting compounds that contain an epoxide group. These angiogenic inhibiting compounds can be administered to a human or animal alone or with epoxide hydrolase inhibiting compounds.

The present invention is especially useful for treating certain ocular neovascular diseases such as macular degeneration.

The compounds which are contemplated as part of the present invention preferably can be given orally to the patient and thereby halt the progression of the disease. Other disease that can be treated using the present invention are diabetic retinopathy, neovascular glaucoma and retrolental fibroplasia.

Accordingly, it is an object of the present invention to provide a compound and method to inhibit unwanted angiogenesis in a human or animal.

It is yet another object of the present invention to provide a composition of inhibiting angiogenesis by oral administration of the composition.

It is another object of the present invention to provide a treatment for diseases mediated by angiogenesis.

It is yet another object of the present invention to provide a treatment for macular degeneration.

It is yet another object of the present invention to provide a treatment for all forms of proliferative vitreoretinopathy including those forms not associated with diabetes.

It is yet another object of the present invention to provide a treatment for solid tumors.

It is yet another object of the present invention to provide a method and composition for the treatment of blood-born tumors such as leukemia.

It is another object of the present invention to provide a method and composition for the treatment of hemangioma.

It is another object of the present invention to provide a method and composition for the treatment of retrolental fibroplasia.

It is another object of the present invention to provide a method and composition for the treatment of psoriasis.

It is another object of the present invention to provide a method and composition for the treatment of Kaposi's sarcoma.

It is another object of the present invention to provide a method and composition for the treatment of Crohn's diseases.

It is another object of the present invention to provide a method and composition for the treatment of diabetic retinopathy.

Other features and advantages of the invention will be apparent from the following description of preferred embodiments thereof.

These and other objects, features and advantages of the present invention will become apparent after a review of the following detailed description of the disclosed embodiments and the appended claims.

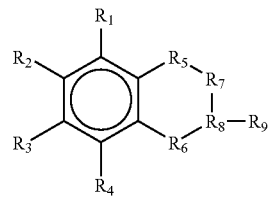

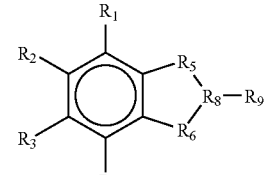

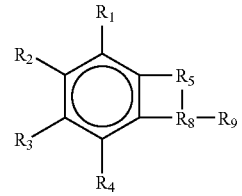

Figure 4:
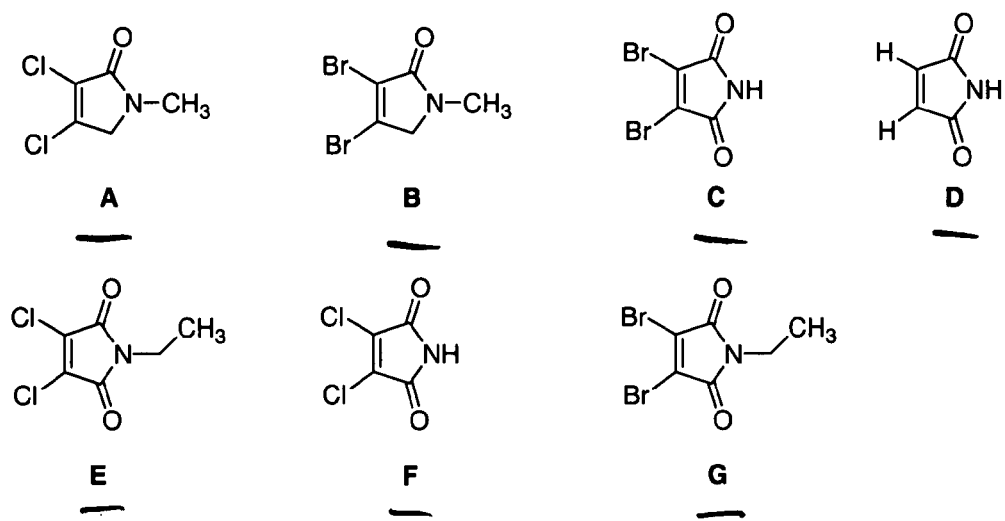

FIG. 4 is a listing of representative compounds in the genus represented by the following general formula:

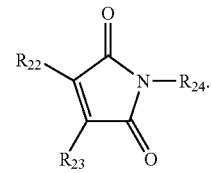

Figure 5:
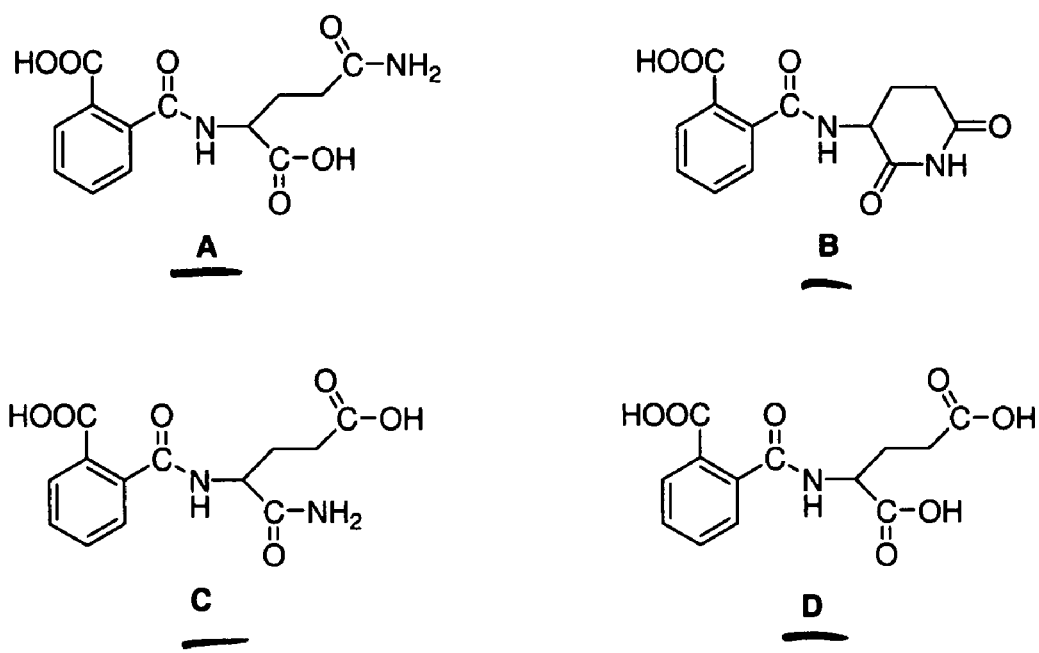

FIG. 5 is a listing of representative compounds in the genus represented by the following general formula:

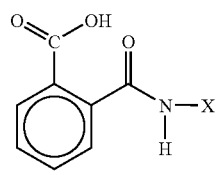

Figure 6:
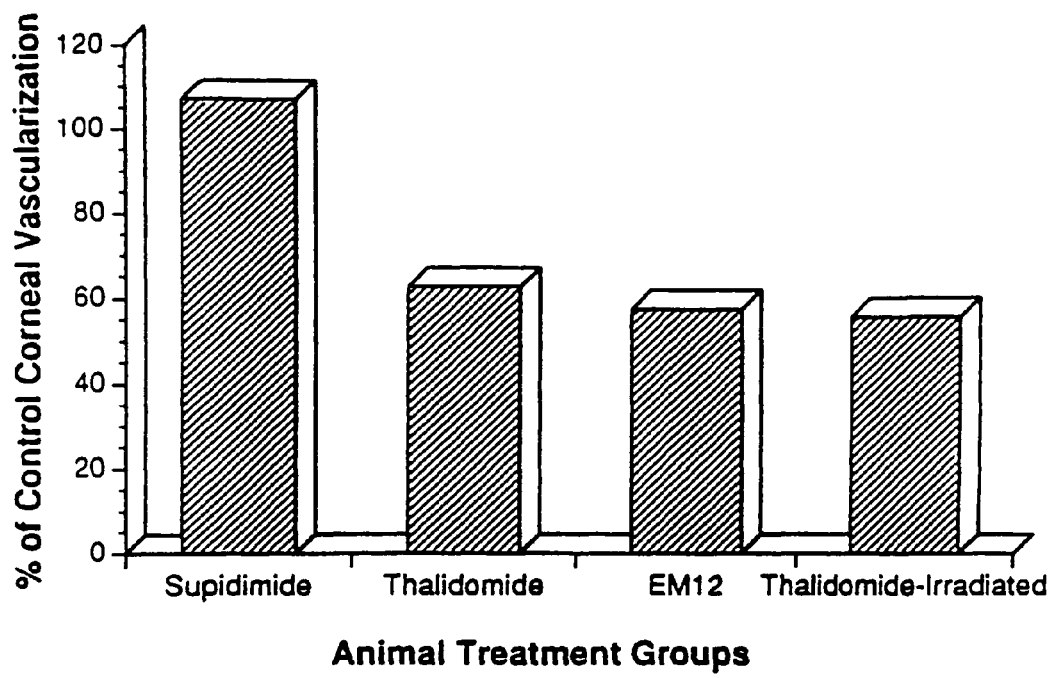

FIG. 6 shows the effect of thalidomide and EM12 on angiogenesis in a rabbit cornea model of angiogenesis.

Figure 7:
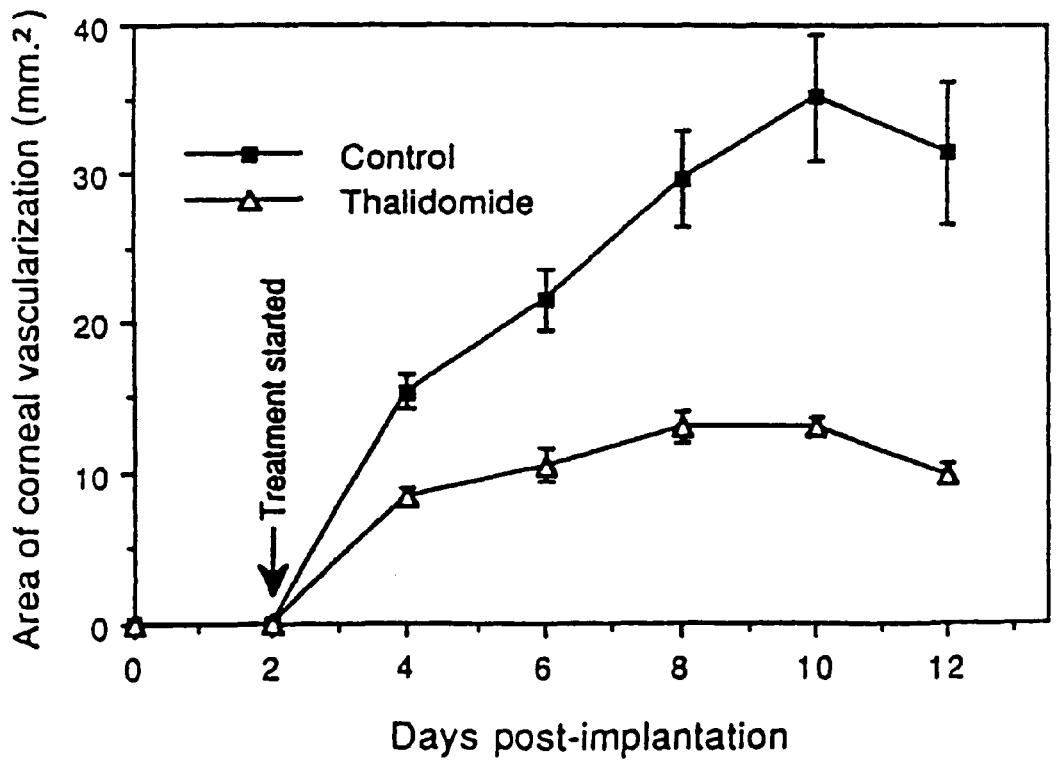

FIG. 7 shows the effect of thalidomide on the area of corneal vascularization in a rabbit cornea model of angiogenesis.

DETAILED DESCRIPTION

The present invention includes compositions and methods for the treatment of diseases that are mediated by angiogenesis. One embodiment of the present invention is the use of thalidomide or the metabolites of thalidomide as disclosed herein to inhibit unwanted angiogenesis. The present invention also includes compounds which cause dysmelia in the developing fetus and have anti-angiogenic activity. The present invention comprises a method of treating undesired angiogenesis in a human or animal comprising the steps of administering to the human or animal with the undesired angiogenesis a composition comprising an effective amount of a teratogenic compound that is anti-angiogenic.

Compounds that can be used in accordance with the present invention include compounds included in the following general formulae. Examples of compounds that have anti-angiogenic properties having one of the following three formulae (A), (B), or (C):

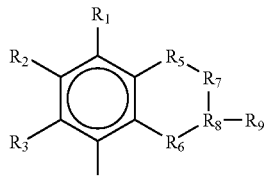
A)

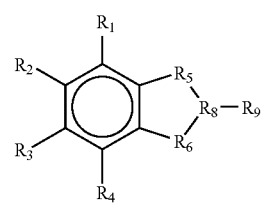
B)

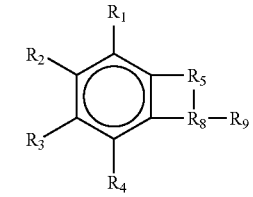
C)

In the above formulae A), B), and C), $R_1$, $R_2$, $R_3$ and $R_4$ can be selected from: —H; —OH; =O, straight chained and branched alkanes, alkenes, alkynes; cyclic alkanes, alkenes, and alkynes; combinations of cyclic and acyclic alkanes, alkenes, and alkynes; alcohol, aldehyde, ketone, carboxylic acid, ester, or ether moieties in combination with acyclic, cyclic, or combination acyclic/cyclic moieties; aza; amino; —XOn or —O—XO$_n$, [where X=N and n=2; X=S and n=2 or 3; or X=P and n=1-3]; and halogens; $R_5$, $R_6$, $R7$, and $R_8$ are each independently selected from:

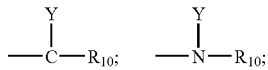

or —O— where Y is optional and is the same as defined above for $R_1$; and $R_{10}$ is the same as defined above for $R_1$, or (where Y is absent) $R_{10}$ is =O; and $R_9$ is a moiety having formula D), E), F), G) or H):

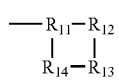
D)

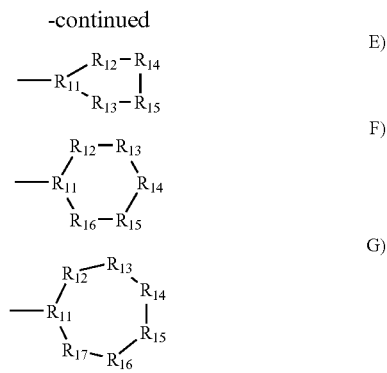

where each of $R_{11}$-$R_{17}$ is (independently) the same as defined above for $R_5$;

H)

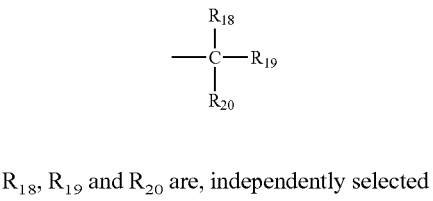

where $R_{18}$, $R_{19}$ and $R_{20}$ are, independently selected from

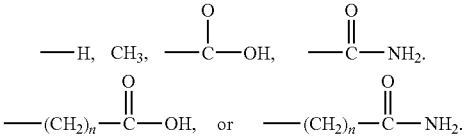

and n=1 to 4.

Accordingly, another aspect of the present invention features inhibiting angiogenesis in a mammal by administering a therapeutic composition comprising one of the above-described compounds in a dosage sufficient to inhibit angiogenesis.

Figure 1:
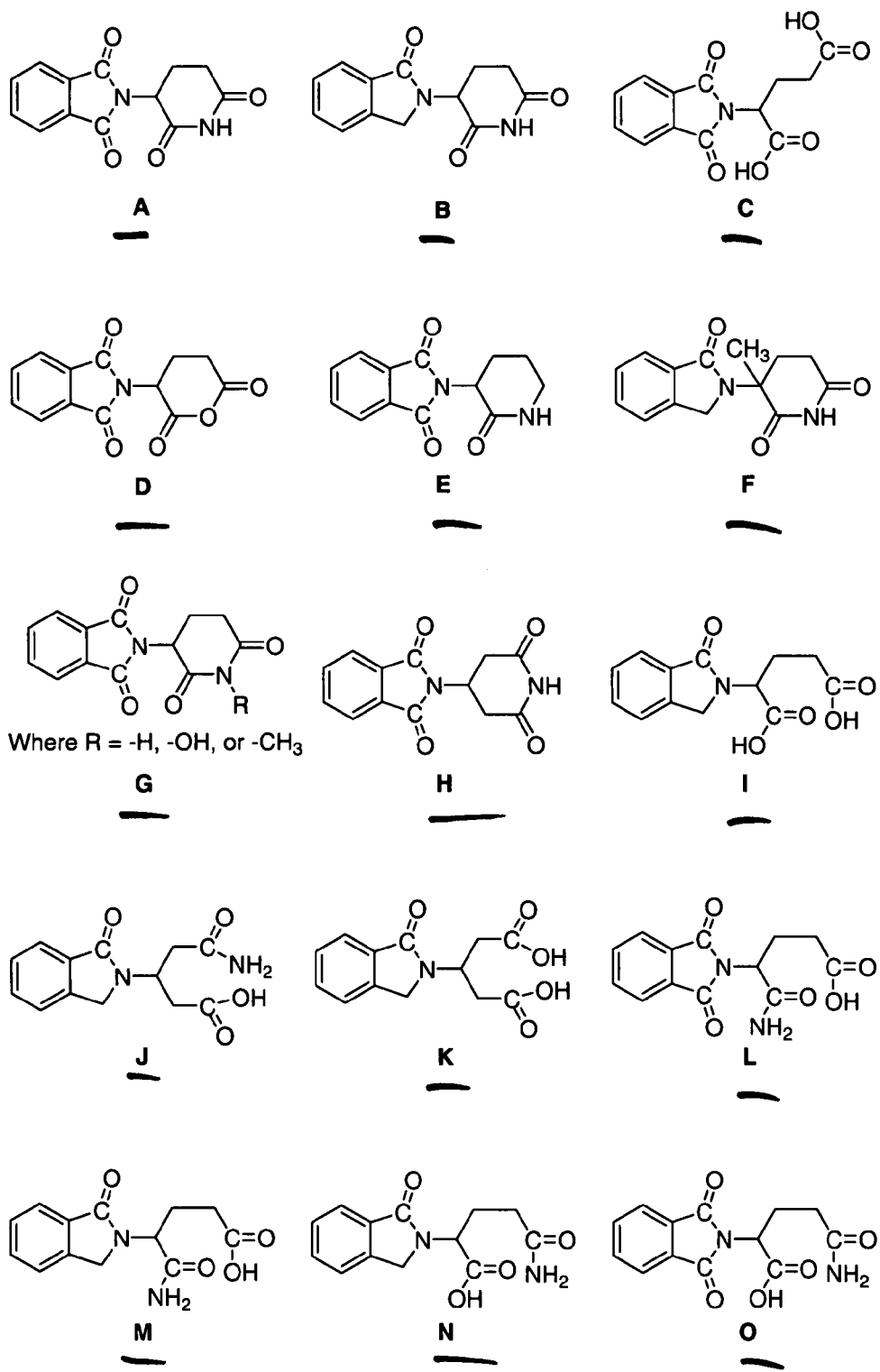
FIGS. 1 through 3 are a listing of representative compounds in the genus represented by the following general formulas.
Figure 2:
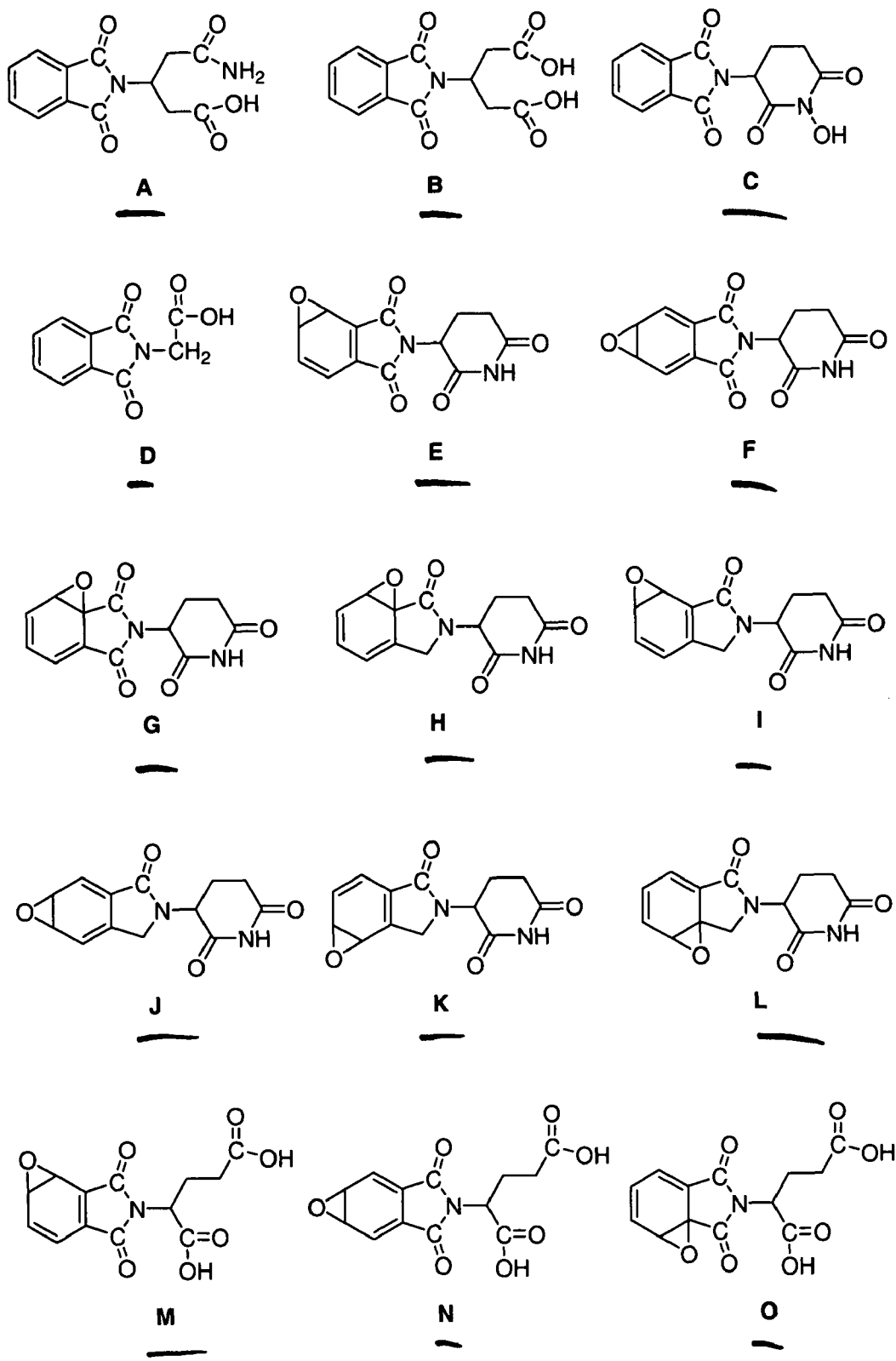
Figure 3:
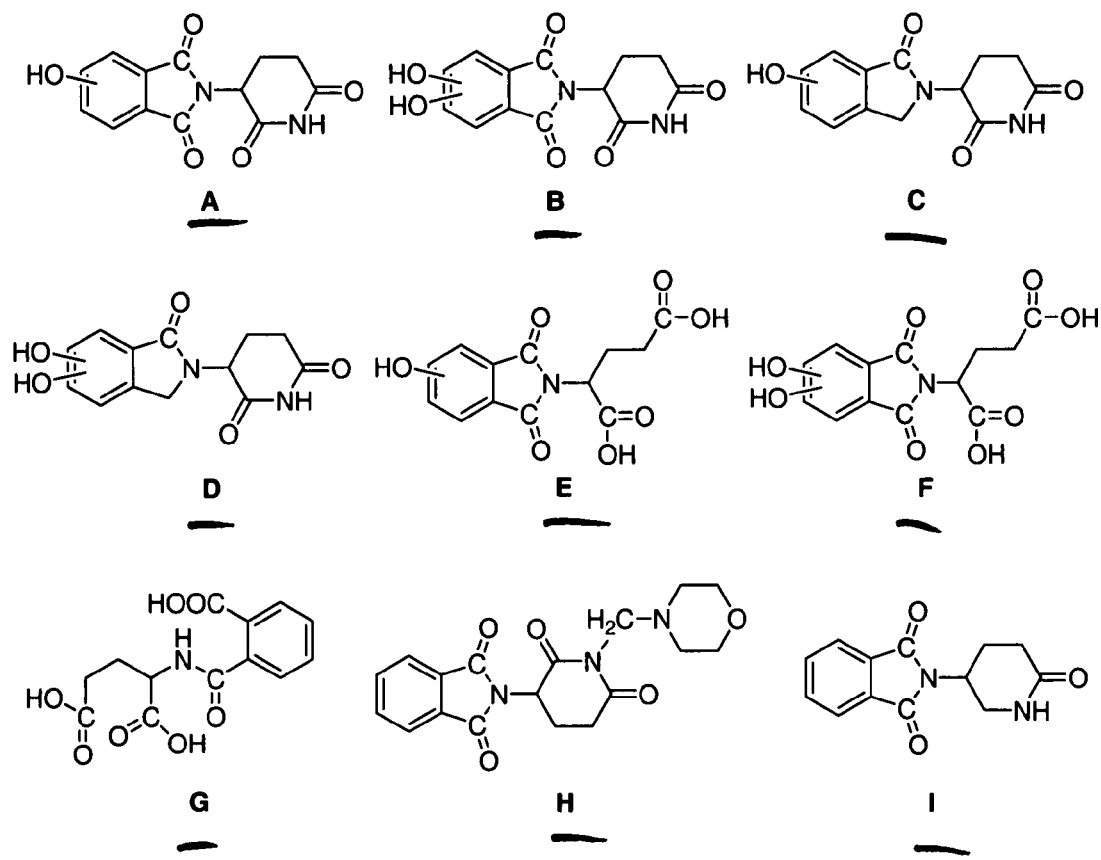

In preferred embodiments, the compound has formula B), where $R_5$ and $R_6$ are selected from the group consisting of:

and $R_9$ has formula F) or H); and $R_{14}$ and $R_{16}$ are selected from the group consisting of:

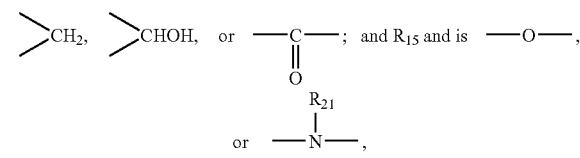

where $R_{21}$ is —H, —CH$_3$, or —OH. Specific preferred compounds according to this aspect of the present invention include thalidomide, its precursors, metabolites and analogs. Particular analogs include EM-12, N-phthaloyl-DL-glutamic acid (PGA) or N-phthaloyl-DL-glutamine anhydride. Examples of compounds that are members of this genus are listed in FIGS. 1 through 3. It is to be understood that the compounds included as part of the present invention are not to be limited to those compounds shown in FIGS. 1 through 3 and include all other compounds that are members of the genus described by the general formulas herein.

Compounds of the following formula that have anti-angiogenic properties:

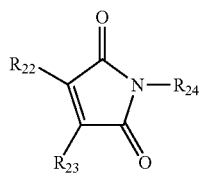

where $R_{22}$ and $R_{23}$ are (independently), —H, —F, —Cl, —Br, —I, —$CH_3$, or —$CH_2$—$CH_3$; and $R_{24}$ is —H, —$CH_3$, or —$CH_2$—$CH_3$.

The present invention also features inhibiting angiogenesis in a mammal by administering a compound according to the above formulae in a dosage sufficient to inhibit angiogenesis. Examples of specific compounds that are members of this genus are listed in FIG. 4.

Angiogenesis inhibition hydrolysis products of thalidomide having the following general formula can be used in practicing the present invention:

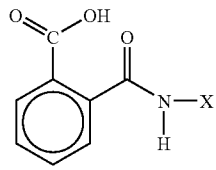

where X is $R_6$ as defined above, or

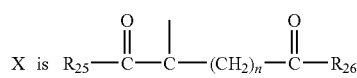

and $R_{25}$ and $R_{26}$ are, independently, —OH, —H, or $NH_2$, and n=1 through 4. Examples of such compounds are shown in FIG. 5.

Angiogenesis inhibition compounds having the following general formula can be used in practicing the present invention:

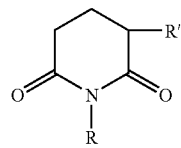

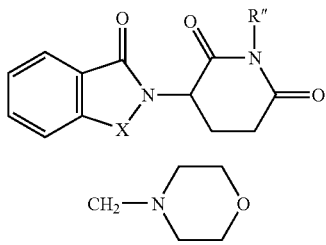

wherein compounds of structure (I), wherein R is selected from the group consisting of hydrogen, alkyl radicals of 1 to 6 carbon atoms, the phenyl radical, and the benzyl radical; and wherein R' is selected from the group consisting of the phthalimido radical and the succinimido radical and of structure (II), wherein X is $CH_2$ or C=O; R" is H, —$CH_2CH_3$, —$C_6H_5$, —$CH_2C_6H_5$, —$CH_2CH$=$CH_2$, or (a) and hydrolysis products of the compounds wherein R" is H and the piperidino ring or both the piperidino and the imido ring are hydrolyzed.

Another set of compounds that are considered part of the present invention are the epoxides of thalidomide, EM-12 and EM-138. Representative epoxide compounds are shown as follows:

Epoxides of thalidomide

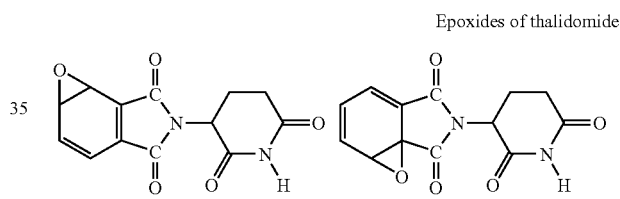

Epoxides of EM 12

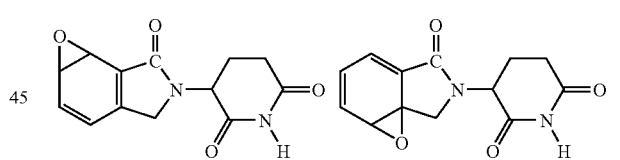

Epoxides of EM 138

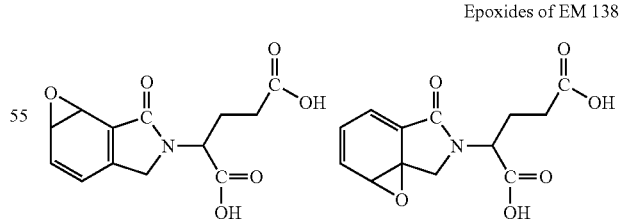

It should be understood that the epoxide can be attached at the 6,1 site on the benzene ring, the 1,2 site, the 2,3 site 3,4 or the 4,5 site. All of these compounds are contemplated as part of the present invention.

The epoxides of the thalidomide, EM-12, and EM 138 can be hydrolized to the following compounds:

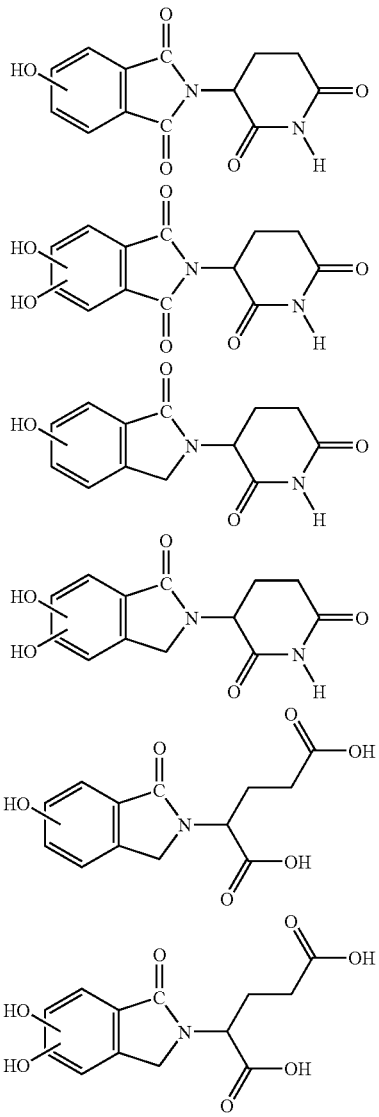

It is to be understood that the hydroxyl group can be on carbons 1, 2, 3, 4, 5 and 6 of the benzene ring. Also contemplated as part of the present invention are dihydroxyl compounds wherein the two hydroxyl groups are located bis to each other on carbons 1, 2, 3, 5 and 6 of the above compounds. The epoxides, the hydrolysis products of the epoxides, and the hydrolysis products of the thalidomide are all contemplated to be part of the present invention.

It is known that epoxides are hydrolized by a group of enzymes known as epoxide hydrolases. There is a class of compounds which are epoxide hydrolase inhibitors. Examples of these compounds are valpromide (2-propylpentanamide) and valproic acid (2-propylpentanoic acid). Because epoxides are important angiogenesis inhibitors, it is contemplated as part of the present invention, compositions comprising any of the angiogenesis inhibitors compounds recited herein in combination with epoxide hydrolase inhibitors. The epoxide hydrolase inhibitors can be administered to a human or animal together or sequentially. The epoxide group appears to be an important substituent common to several angiogenesis inhibitors. The use of epoxide hydrolase inhibitors to potentiate the activity of any angiogenesis inhibitor containing an epoxide is contemplated as part of the present invention. For example, the epoxide hydrolase inhibitors can be administered with the following epoxide-containing anti-angiogenesis compounds: AGM 1470, Eponimycin, microbial metabolites of *Scolecobasidium arenarium* designated f/2015, fr/111142 and fr/18487. See Oikawa. *Biochem Biophys. Res. Comm*, Vol. 81:1070 (1971) and Otsuka, *J. Microbial. Biotech.*, Vol 1:163 (1991).

It is contemplated as an embodiment of the present invention the use of the epoxide containing angiogenesis inhibitors with or without epoxide hydrolase inhibitors as a treatment for diseases mediated by elevated or toxic levels of TNF-α. TNF-α has been recognized as manifesting a dose dependent toxicity. If present at low levels for a long period of time, TNF-α can result in cachexia. Cachexia is a general weight loss and wasting occurring in the course of some chronic diseases such as cancer, opportunistic infections of AIDS, inflammatory diseases, parasitic diseases, tuberculosis, and high dose IL-2 therapy. The epoxide containing angiogenesis inhibitors, with or without epoxide hydrolase inhibitors, are also effective in treating diseases such as septic shock, leprosy and graph vs. host disease.

Other embodiments are within the present invention. For example, other dysmelia-causing compounds can be used according to the present invention, e.g. 4-methylphthalic acid, pyridoxine, vasopressin, acetazolamide, or a compound having the following formula (where R=H, —OH, or —CH₃):

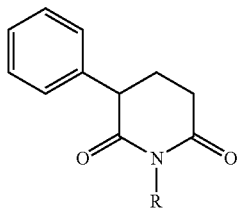

Other compounds which are teratogens, such as valproic acid (2-propylpentanoic acid), the retinoids, such as cis-retinoic acid, and rifampin may also be used in accordance with the invention.

In summary, the preferred compounds are thalidomide, as well as analogs, hydrolysis products, metabolites and precursors of thalidomide that are teratogenic, and, more specifically, that cause dismelia. However, it is to be understood that it is not necessary for a compound to have both teratogenic activity and angiogenesis inhibiting activity to be considered part of the present invention. Dysmelia-causing compounds can be identified by the general procedures of Helm, *Arzneimittle-forschung*, 31(i/6):941-949 (1981), in which rabbit pups are examined after exposure to the compound in utero. The compounds can generally be purchased, e.g., from Andrulis Pharmaceuticals, Beltsville, Md., or synthesized according to known procedures. It is to be understood that the compounds of the present invention can exist as enantiomers and that the racemic mixture of enantiomers or the isolated enantiomers are all considered as within the scope of the present invention.

Many of the compounds that are contemplated as part of the present invention can be enriched in optically active enantiomers of the compounds specified above. Specifically, Blaschke has reported that the S enanantiomers may be disproportionately responsible for the dismelia-producing effect of these compounds. See, generally Blaschke, *Arzneimittelforschung* 29:1640-1642 (1979). The above described articles generally describe procedures to obtain optically active preparations of the compounds of interest. See, e.g. Shealy et al., *Chem. Indus.* 1030 (1965); and Casini et al. *Farmaco Ed. Sci.* 19:563 (1964).

The compounds described above can be provided as pharmaceutically acceptable formulations using formulation methods known to those of ordinary skill in the art. These formulations can be administered by standard routes. In general, the combinations may be administered by the topical, transdermal, oral, rectal or parenteral (e.g., intravenous, subcutaneous or intramuscular) route. In addition, the combinations may be incorporated into biodegradable polymers allowing for sustained release of the compound, the polymers being implanted in the vicinity of where drug delivery is desired, for example, at the site of a tumor. The biodegradable polymers and their use are described, for example, in detail in Brem et al., *J. Neurosurg.* 74:441-446 (1991).

The dosage of the compound will depend on the condition being treated, the particular compound, and other clinical factors such as weight and condition of the human or animal and the route of administration of the compound. It is to be understood that the present invention has application for both human and veterinary use. For oral administration to humans, a dosage of between approximately 0.1 to 300 mg/kg/day, preferably between approximately 0.5 and 50 mg/kg/day, and most preferably between approximately 1 to 10 mg/kg/day, is generally sufficient.

The formulations include those suitable for oral, rectal, ophthalmic, (including intravitreal or intracameral) nasal, topical (including buccal and sublingual), vaginal or parenteral (including subcutaneous, intramuscular, intravenous, intradermal, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into associate the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface active or dispersing agent. Molded tablets may be made by molding, in a suitable machine, a mixture of the powdered compound moistened with an inert liquid diluent. The tablets may be optionally coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tamports, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient.

It should be understood that in addition to the ingredients, particularly mentioned above, the formulations of the present invention may include other agents conventional in the art having regard to the type of formulation in question, for example, those suitable for oral administration may include flavoring agents.

Diseases associated with corneal neovascularization that can be treated according to the present invention include but are not limited to, diabetic retinopathy, retinopathy of prematurity, corneal graft rejection, neovascular glaucoma and retrolental fibroplasia, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, trauma, rheumatoid arthritis, systemic lupus, polyarteritis, Wegeners sarcoidosis, Scleritis. Steven's Johnson disease, periphigoid radial keratotomy, and corneal graph rejection.

Diseases associated with retinal/choroidal neovascularization that can be treated according to the present invention include, but are not limited to, diabetic retinopathy, macular degeneration, sickle cell anemia, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications. Other diseases include, but are not limited to, diseases associated with rubeosis (neovasculariation of the angle) and diseases caused by the abnormal proliferation of fibrovascular or fibrous tissue including all forms of proliferative vitreoretinopathy, whether or not associated with diabetes.

Another disease which can be treated according to the present invention is rheumatoid arthritis. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Another disease that can be treated according to the present invention are hemangiomas, Osler-Weber-Rendu disease, or hereditary hemorrhagic telangiectasia, solid or blood borne tumors and acquired immune deficiency syndrome.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE I

The chick embryo chorioallantoic membrane assay described by Crum et al., *Science* 230:1375 et seq. (1985), is used to identify compounds that do not require further metabolic conversion. See also, U.S. Pat. No. 5,001,116, hereby incorporated by reference, which describes the CAM assay at col. 7 of the patent. Briefly, fertilized chick embryos are removed from their shell on day 3 or 4, and a methylcellulose disc containing the compound is implanted on the chorioallantoic membrane. The embryos are examined 48 hours later and, if a clear avascular zone appears around the methylcellulose disc, the diameter of that zone is measured.

EXAMPLE II

Rabbit Cornea Angiogenesis Assay

Pellets for implantation into rabbit corneas were made by mixing 110 μl of saline containing 12 μg of recombinant bFGF (Takeda Pharmaceuticals-Japan) with 40 mg of sucralfate (Bukh Meditec-Denmark); this suspension was added to 80 μl of 12% hydron (Interferon Sciences) in ethanol. 10 μl aliquots of this mixture was then pipetted onto teflon pegs and allowed to dry producing approximately 17 pellets. A pellet was implanted into corneal micropockets of each eye of an anesthetized female New Zealand white rabbit, 2 mm from the limbus followed by topical application of erythromycin ointment onto the surface of the cornea. The animals were fed daily from 2 days post-implantation by gastric lavage with either drug suspended in 0.5% carboxymethyl cellulose or 0.5% carboxymethyl cellulose alone. Thalidomide was purchased from Andrulus Pharmaceutical (Maryland) and the EM-12 and Supidimide were kindly provided by Grunenthal GMBH (Germany). The animals were examined with a slit lamp every other day in a masked manner by the same corneal specialist. The area of corneal neovascularization was determined by measuring with a reticule the vessel length (L) from the limbus and the number of clock hours (C) of limbus involved. A formula was used to determine the area of a circular band segment: $C/12*3.1416 [r^2-(r-L)^2]$ where $r=6$ mm the measured radius of the rabbit cornea. Various mathematical models were utilized to determine the amount of vascularized cornea and this formula was found to provide the most accurate approximation of the area of the band of neovascularization that grows towards the pellet.

It is important to note that the rabbit cornea assay is preferable because it will generally recognize compounds that are inactive per se but are metabolized to yield active compounds. Thalidomide related compounds, as shown below in Example III are known to be teratogens and are candidates for use in the present invention.

EXAMPLE III

Inhibition of bFGF Induced Corneal Neovascularization by Thalidomide and Related Analog Expressed as Percent of Median Control on Day 8

Pellets containing bFGF and sucralfate were implanted into micropockets of both corneas of rabbits according to Example II. Vessel ingrowth into clear cornea from the limbus was first noted on day 2 and treatments (200 mg/kg orally) were begun on this day. The area of corneal neovascularization was measured from day 4 through day 12. Day 8 measurements were used for comparison between groups. No regression of vessels and near maximal neovascularization was seen at this time point. Statistical analysis was performed with ANOVA with ranked data to account for interexperimental variation and to guard against a non-normal distribution of data (i.e. outliers) by utilizing a nonparametric method.

The compounds tested were as follows:

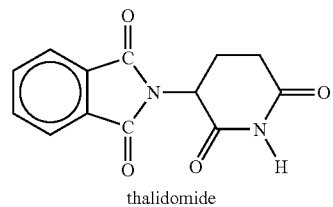
thalidomide

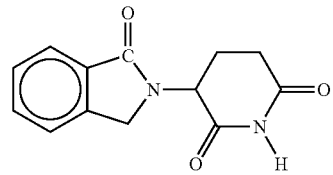
EM-12

-continued

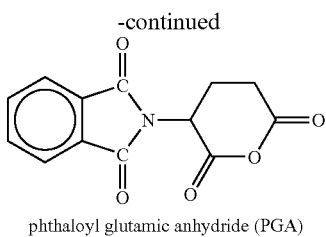

phthaloyl glutamic anhydride (PGA)

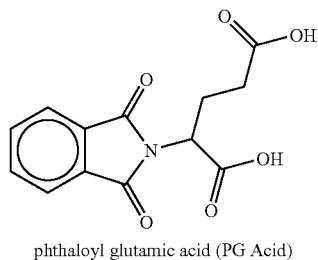

phthaloyl glutamic acid (PG Acid)

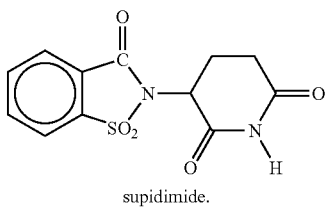

supidimide.

Treatment with a dose of (200 mg/kg) of thalidomide resulted in an inhibition of the area of vascularized cornea that ranged from 30-51% in three experiments with a median inhibition of 36% (FIG. 6) (n=30 eyes, p=0.0001, 2 way ANOVA with ranked data). The inhibition of angiogenesis by thalidomide was seen after only two doses (FIG. 7). The rabbits did not demonstrate obvious sedation and there were no signs of toxicity or weight loss. The teratogenic analog EM-12, which shares the other properties of thalidomide was also inhibitory, with a median inhibition of 42% (n=10 eyes, p=0.002, 1-way ANOVA with ranked data). Supidimide, a nonteratogenic analog of thalidomide that retains the sedative properties of thalidomide, exhibited no activity (area 107% of control, n=10 eyes, not statistically different from control). Other analogs, PGA and PG acid displayed weaker inhibitory effects than thalidomide (data not shown). The density of vessel ingrowth in thalidomide-treated animals was also markedly reduced.

EXAMPLE IV

EM-12 in Rabbit Cornea Assay

EM-12 was tested in the rabbit cornea assay described in Example II at 100 mg/kg/day and showed 21% inhibition, and at 200 mg/kg/day the assay showed 43% inhibition.

EXAMPLE V

Phthaloyl Glutamic Acid in CAM

Phthaloyl glutamic acid was tested in the above described CAM assay and exhibit an avascular zone with a mild scar.

EXAMPLE VI

Phthaloyl Glutamic Acid in Rabbit Cornea Assay

Phthaloyl glutamic acid described above at 200 mg/kg and exhibited 29% inhibition of angiogenesis.

EXAMPLE VII

Phthaloyl Glutamic Anhydride in CAM Assay

Phthaloyl glutamic anhydride was test in the CAM assay described above and exhibited an avascular zone.

It should be understood, of course, that the foregoing relates only to preferred embodiments of the present invention and that numerous modifications or alterations may be made therein without departing from the spirit and the scope of the invention as set forth in the appended claims.

The invention claimed is:

1. A method for inhibiting undesired angiogenesis in a human having a blood born tumor comprising orally administering to said human a capsule comprising an angiogenesis-inhibiting amount of thalidomide and administering an amount of a compound that is an epoxide hydrolase inhibitor.

2. The method of claim 1 wherein the thalidomide is administered in an amount between approximately 0.1 and approximately 300 mg/kg/day.

3. The method of claim 2 wherein the thalidomide is administered in an amount between approximately 0.5 and 50 mg/kg/day.

4. The method of claim 3 wherein the thalidomide is administered in an amount between approximately 1 and approximately 10 mg/kg/day.

5. The method of claim 1 wherein the blood born tumor is leukemia.

6. The method of claim 1, wherein the epoxide hydrolase inhibitor is administered to said human together with thalidomide.

7. The method of claim 1, wherein the thalidomide and the epoxide hydrolase inhibitor are administered to said human sequentially.

* * * * *

UNITED STATES PATENT AND TRADEMARK OFFICE
CERTIFICATE OF CORRECTION

PATENT NO. : 7,723,361 B2
APPLICATION NO. : 11/096155
DATED : May 25, 2010
INVENTOR(S) : Robert J. D'Amato It is certified that error appears in the above-identified patent and that said Letters Patent is hereby corrected as shown below:

On the Title Page, in item (73) "Assignee," please revise as follows:

-- (73) Assignee: ~~Celgene Corporaration, Summit, NJ (US)~~
The Children's Medical Center Corporation, Boston MA (US) --

Signed and Sealed this

Seventeenth Day of August, 2010

David J. Kappos
*Director of the United States Patent and Trademark Office*